United States Patent
Dosho et al.

(10) Patent No.: US 7,443,952 B2
(45) Date of Patent: Oct. 28, 2008

(54) X-RAY DIFFRACTION MEASUREMENT METHOD AND X-RAY DIFFRACTION APPARATUS

(75) Inventors: Akihide Dosho, Tokyo (JP); Koji Kakefuda, Tokyo (JP)

(73) Assignee: Rigaku Corporation, Akishima-Shi, Tokyo (JP)

( * ) Notice: Subject to any disclaimer, the term of this patent is extended or adjusted under 35 U.S.C. 154(b) by 0 days.

(21) Appl. No.: 11/868,659

(22) Filed: Oct. 8, 2007

(65) Prior Publication Data

US 2008/0084964 A1 Apr. 10, 2008

(30) Foreign Application Priority Data

Oct. 6, 2006 (JP) ............................. 2006-275846

(51) Int. Cl.
*G01N 23/20* (2006.01)

(52) U.S. Cl. ............................. 378/71; 378/81; 378/84

(58) Field of Classification Search .............. 378/70–90
See application file for complete search history.

(56) References Cited

U.S. PATENT DOCUMENTS 3,852,594 A 12/1974 Paolini

FOREIGN PATENT DOCUMENTS

JP 50-063982 5/1975

OTHER PUBLICATIONS

Cullity, B.D., "Elements of X-ray diffraction, New Edition," KK Agne, Mar. 25, 1989, translated by Gentaro Matsumura (in Japanese).
Cullity, B.D., "Elements of X-ray diffraction, Second Edition," Addison-Wesley Series in Metallurgy and Materials, Chapter 7, 1978, pp. 188-199, Addison-Wesley Publishing Company, Inc. (in English).

*Primary Examiner*—Courtney Thomas
(74) *Attorney, Agent, or Firm*—Buchanan Ingersoll & Rooney PC

(57) ABSTRACT

Disclosed is an X-ray diffraction apparatus that irradiates a sample with X-ray emitted from an X-ray source by resting the X-ray using a divergence slit and detects diffracted X-ray generated from the sample using an X-ray detector. The divergence angle of the divergence slit is a fixed value, and the divergence slit is a slit that restricts the X-ray irradiation width in the sample width direction. The sample is arranged in a longitudinally-elongated manner in which its sample width is smaller than a standard sample width and its sample height is the same as a standard sample height. X-ray intensity calculated based on an output of the X-ray detector is compensated based on an effective divergence angle calculated based on the sample width to thereby obtain true X-ray intensity.

17 Claims, 15 Drawing Sheets

(LATERALLY-ELONGATED ARRANGEMENT)

(LONGITUDINALLY-ELONGATED ARRANGEMENT)

DIFFRACTION ANGLE DEPENDENCE OF DIFFRACTED X-RAY INTENSITY

X-RAY DIFFRACTION MEASUREMENT METHOD AND X-RAY DIFFRACTION APPARATUS

BACKGROUND OF THE INVENTION

1. Field of the Invention

The present invention relates to an X-ray diffraction measurement method and an X-ray diffraction apparatus both for performing X-ray diffraction measurement by use of a fixed divergence slit.

2. Description of the Related Art

Generally, in an X-ray diffraction measurement, X-ray emitted from an X-ray source is applied to a sample at an incident angle "θ", and diffracted X-ray emitted from the sample at a diffraction angle "2θ" is detected by an X-ray detector, and intensity I of the diffracted X-ray is calculated based on an output signal of the X-ray detector. Diffraction angle "2θ" is always an angle double the incident angle "θ". Given that diffracted X-ray intensity I is a function of the X-ray incident angle "θ", the diffracted X-ray intensity can be expressed by I(θ). On the other hand, given that diffracted X-ray intensity I is a function of diffraction angle "2θ", the diffracted X-ray intensity can be expressed by I(2θ). In the present specification, the expression of I(θ) is frequently used for convenience' sake.

In the above X-ray diffraction measurement, X-ray emitted from the X-ray source is irradiated on the sample with its size in the sample width direction restricted by a divergence slit (DS). A method in which X-ray diffraction measurement is performed with the slit width (that is the divergence angle) of the divergence slit being fixed has widely been known. For example, section 7-3 "X-ray optics" in page 178 (7-th chapter "Diffractometer and Spectrometer Measurements") of "Elements of X-ray diffraction, New Edition" (written by B. D. Cullity and translated by Gentaro Matsumura, issued from KK AGNE, Mar. 25, 1989, 7-th edition) discloses that the spread angle (i.e., divergence angle) of a commonly used divergence slit is "1°", that is, divergence angle is set to a fixed value.

Further, Japanese Unexamined Patent Application Publication No. S50-63982, in column of Prior Art and FIG. 1 (corresponding description is shown in page 2), discloses that the divergence angle of the divergence slit is set to a fixed value. Hereinafter, in the present specification, a divergence slit whose divergence angle is set to a fixed value is referred to as "fixed divergence slit" and a divergence slit whose divergence angle is variable is referred to as "variable divergence slit".

Conventionally, in X-ray diffraction measurement using the fixed divergence slit, a sample S is disposed at a standard sample area, which is defined by standard sample width Wr×standard sample height Hr, as shown in FIGS. 6A and 6B. In a typical X-ray diffraction apparatus, setting is made such that Wr=Hr=20 mm. FIG. 6B is a cross-sectional view taken along $Z_6$-$Z_6$ line of FIG. 6A. As shown in FIGS. 6A and 6B, X-ray emitted from an X-ray source F is irradiated on the sample S with the divergence thereof restricted by a divergence slit 101. When diffracted X-ray is generated from the sample S, the diffracted X-ray is detected by an X-ray detector 102.

X-ray applied to the sample S is shown rectangularly by a chain line surrounding the sample S in FIG. 6A. The width $W_0$ of X-ray applied to the sample S is determined by divergence angle "β" of the divergence slit 101 and X-ray incident angle "θ". The width $W_0$ is referred to as "X-ray irradiation width" hereinafter. FIG. 6B shows a case where X-ray incident angle θ is a low angle. In this case, X-ray irradiation width $W_0$ is larger than standard sample width Wr. FIG. 7C is a case where X-ray incident angle θ is the boundary angle between a low angle and high angle. In this case, X-ray irradiation width $W_0$ is equal to sample width. The sample width in FIG. 7C is the standard sample width Wr. FIG. 7D shows a case where X-ray incident angle θ is a high angle. In this case, X-ray irradiation width $W_0$ is smaller than standard sample width Wr.

In FIG. 6A, the height of X-ray applied to the sample S, that is the length of the X-ray in a direction perpendicular to the X-ray irradiation width $W_0$, is illustrated to be larger than the standard sample height Hr for clearly showing them. Actually, the height of X-ray applied to the sample S is substantially same as the standard sample height Hr. Such a condition of the height of X-ray applied to the sample S against the standard sample height Hr also applies to FIGS. 8A, 8B, and 9A, respectively.

In the present specification, the sample disposed in the aforesaid standard sample area is hereinafter referred to as "standard-arrangement sample". When X-ray diffraction measurement is performed using the fixed divergence slit for the standard-arrangement sample, X-ray incident angle θ is moved from a low angle region shown in FIG. 6B to a high angle region shown in FIG. 7D while the surface of the sample S is scanned with X-ray, and the diffracted X-ray from the sample S is detected by the X-ray detector 102 during the scanning operation.

There may a case where a sufficient amount of sample cannot be prepared for actual X-ray diffraction measurement. In this case, it is impossible to fill up the entire standard sample area (Wr×Hr) shown in FIG. 6A with the sample S. In order to cope with such a case in which the amount of the sample is insufficient, two arrangement methods of the sample shown in FIGS. 8A and 8B are available.

The first method shown in FIG. 8A is a method in which the sample width is made equal to standard sample width Wr and the sample height Hs is made smaller than standard sample height Hr. In the present specification, this arrangement is referred to as "laterally-elongated arrangement". On the other hand, the second method shown in FIG. 8B is a method in which the sample width Ws is made smaller than standard sample width Wr and the sample height is made equal to standard sample height Hr. In the present specification, this arrangement is referred to as "longitudinally-elongated arrangement".

In the case of the laterally-elongated arrangement shown in FIG. 8A, a relationship between X-ray irradiation width $W_0$ and sample width Wr in the course of change in X-ray incident angle θ (see FIG. 6B) is the same as that in the case of the standard-arrangement sample which is shown in FIGS. 6B, 7C, and 7D. That is, in this case, the X-ray irradiation width falls equal to or smaller than the sample width in a wide range of the diffraction angle 2θ. The amount of X-ray applied to the sample is constant in the region within which the X-ray irradiation width falls equal to or smaller than the sample width, and relative X-ray intensity (i.e., intensity ratio) of a peak existing in this range is measured correctly. In the diffraction angle region within which the irradiation width exceeds the sample width, the relative intensity decreases since the amount of effective X-ray is reduced.

The relative X-ray intensity of a peak means a ratio of observed X-ray intensity relative to "true" X-ray intensity. The "true" X-ray intensity means X-ray intensity observed in the diffraction angle region within which the X-ray irradiation width falls equal to or smaller than the sample width. That is, when the X-ray irradiation width is within the sample width, an X-ray intensity having the same strength as that of the true X-ray intensity is observed.

In the case of the longitudinally-elongated arrangement, as can be understood from FIGS. 9B, 10C and 10D, X-ray irradiation width $W_0$ runs off sample width Ws even when X-ray incident angle θ is a relatively high angle. When X-ray irradiation width $W_0$ runs off sample width Ws, X-ray is applied to unnecessary portion outside the sample width and, accordingly, the amount of X-ray applied to the sample width is reduced, with the result that the relative X-ray intensity of a peak of the diffracted X-ray is reduced to prevent correct determination of a peak of the diffracted X-ray.

Under such circumstances, when X-ray diffraction measurement is performed for a sample of insufficient amount, those skilled in the art in the field of X-ray measurement generally select the laterally-elongated arrangement in which a correct and constant relative X-ray intensity (namely intensity ratio) in a wide range of the diffraction angle 2θ can be maintained. However, in the case where the laterally-elongated arrangement is adopted, the X-ray irradiation height always runs off sample height Hs in FIG. 8A. This reduces the amount of sample that can contribute to diffraction, thus posing a problem in that a sufficient diffracted X-ray intensity cannot be obtained especially on the high angle side of the X-ray incident angle θ. In order to obtain a sufficient diffracted X-ray intensity in this situation, measurement needs to be performed for a very extended period of time. This is unrealistic.

SUMMARY OF THE INVENTION

The present invention has been made in view of the above situation, and an object thereof is to provide an X-ray diffraction measurement method and an X-ray diffraction apparatus capable of obtaining a sufficient diffracted X-ray intensity in 2θ-high angle region in which the diffracted X-ray intensity becomes weak and capable of maintaining the relative X-ray intensity (meaning intensity ratio) of a peak of diffracted X-ray in 2θ-middle angle region and 2θ-low angle region in which the X-ray irradiation width becomes wider to thereby obtain correct diffracted X-ray data in the case where a sample of smaller amount than the standard-arrangement sample amount is used as a measurement target.

An X-ray diffraction measurement method according to the present invention that (1) irradiates a sample with X-ray emitted from an X-ray source while restricting the X-ray using a divergence slit and detects diffracted X-ray generated from the sample using X-ray detector; wherein (2) the divergence angle of the divergence slit is a fixed value; (3) the divergence slit is a slit that restricts X-ray irradiation width in the sample width direction; (4) the sample is arranged in a longitudinally-elongated manner in which its sample width is smaller than a standard sample width and its sample height is the same as a standard sample height; and (5) X-ray intensity calculated based on an output of the X-ray detector is compensated based on an effective divergence angle calculated based on the sample width.

According to the method of the present invention, a fixed divergence slit is used as the divergence slit, thereby simplifying the configuration and reducing cost as compared to a case where a variable divergence slit is used. Further, measurement is performed with the sample arranged in a longitudinally-elongated manner (see FIG. 8B), so that diffracted X-ray with a higher intensity can be obtained in 2θ high angle region (e.g., 80° or more) as compared to a case where the sample is arranged in a laterally-elongated manner (see FIG. 8A) even if the amount of the sample is small, thereby obtaining correct diffraction data in a short period of time.

In the case of the longitudinally-elongated arrangement, X-ray irradiation width runs off the sample width not only in low 2θ-angle region (e.g., 20° or less) but also in middle 2θ-angle region (e.g., about 60°). This prevents relative X-ray intensity (intensity ratio) of diffracted X-ray from being constant, thereby making a difference from the case where a standard-arrangement sample is used. As a result, it is impossible to obtain correct diffracted X-ray intensity. Therefore, even if qualitative analysis is performed by comparing a diffraction profile calculated by measurement performed for the sample of longitudinally-elongated arrangement with standard data [e.g., ICDD (International Centre for Diffraction Data) card data] previously calculated with respect to the standard sample, correct analysis cannot be performed.

In order to cope with this problem, in the present invention, X-ray intensity $I_{obs}$ calculated based on the output of the X-ray detector is compensated based on an effective divergence angle of the divergence slit calculated from the sample width. This allows a decrease in the relative X-ray intensity (intensity ratio) in the 2θ low angle region, which is exhibited in the sample S arranged in a longitudinally-elongated manner, to be compensated, enabling the relative X-ray intensity to be maintained at a constant value. That is, it is possible to approximate the intensity ratio characteristic to that obtained with respect to the standard-arrangement sample. Thus, a correct analysis result can be obtained in qualitative analysis being performed by comparing a diffraction profile of the sample having a small sample width with a standard diffraction profile of the sample having the standard sample width.

An example of the "effective divergence angle calculated from sample width" will next be described. Assuming in FIG. 11 that the sample width of the sample S is "2A", X-ray incident angle for the sample S is "θ", and radius of a goniometer is "R", it is preferable to calculate the effective divergence angle "β" according to the following expression:

$$\tan \beta = (\sin \theta)/(R/2A) \quad (1)$$

and, assuming in FIG. 11 that the actual divergence angle of the divergence slit 2 is "γ" and X-ray intensity calculated based on an output of the X-ray detector 10 is $I_{obs}(\theta)$, it is preferable to calculate true X-ray intensity $I_{tru}(\theta)$ according to the following expression:

$$I_{tru}(\theta) = (\gamma/\beta)I_{obs}(\theta) \quad (2).$$

Although the value of the actual goniometer radius "R" differs depending on the type of the goniometer, typical value thereof is 185 mm or 150 mm.

The above expression (2) is effective when $$\beta \leq \gamma \quad (3)$$

is satisfied, that is, when the effective divergence angle β of the divergence slit is equal to or smaller than the actual divergence angle γ of the divergence slit. (⅙)°, (½)°, 1°, 2°, 4°, and the like are used as the actual divergence angle γ at present. One of the above values is selected, depending on in which region of the diffraction angle 2θ the diffracted X-ray from the sample to be measured appears.

Another example of the "effective divergence angle calculated from sample width" will next be described. Assuming in FIG. 12 that the sample width of the sample S is "2A", X-ray incident angle for the sample S is "θ", and radius of a goniometer is "R", it is preferable to calculate effective divergence angle part "β1" of the effective divergence angle "β" which is on the side farther away from the X-ray source F with respect to sample width center C and effective divergence angle part "β2" of the effective divergence angle "β" on the side nearer to the X-ray source F with respect to the sample width center C according to the following expressions:

$$\tan \beta 1 = (\sin \theta)/\{(R/A) - \cos \theta\} \quad (4)$$

$$\tan \beta 2 = (\sin \theta)/\{(R/A) + \cos \theta\} \quad (5)$$ and, assuming in FIG. 12 that the actual divergence angle of the divergence slit 2 is "γ" and X-ray intensity calculated based on an output of the X-ray detector 10 is $I_{obs}(\theta)$, it is preferable to calculate true X-ray intensity $I_{tru}(\theta)$ according to the following expression:

$$I_{tru}(\theta) = \{\gamma/(\beta 1 + \beta 2)\} \times I_{obs}(\theta) \quad (6).$$

The above expression (6) is effective, when $$\beta 1, \beta 2 \leq \gamma/2 \quad (7)$$

is satisfied, that is, when both the effective divergence angle parts β1 and β2 are equal to or smaller than the half of the actual divergence angle γ (i.e., γ/2).

In the identification method of the effective divergence based on FIG. 12, a calculation method of the effective divergence angle is differentiated between one half-part on the side farther away from the X-ray source F with respect to the sample width center C and other half-part on the side nearer to the X-ray source F with respect to the sample width center C. Note that one half-part on the side farther away from the X-ray source F with respect to the sample width center C may also be referred to as "right side of the sample" in brief, and other half-part on the side nearer to the X-ray source F with respect to the sample width center C may also be referred to as "left side of the sample" in brief. The reason for this is that when X-ray incident angle θ changes, the amount of X-ray irradiation that runs off the sample width on the right side of the sample S and amount of X-ray irradiation that runs off the sample width on the left side of the sample S differ from each other. By calculating the effective divergence angle with the sample width 2A separated into two parts at the center C as described above, more correct intensity compensation can be achieved as compared to the calculation method based on FIG. 11.

FIG. 13 shows, by using a graph, that the X-ray irradiation width defined by the divergence slit exhibits asymmetric characteristics between the right and left parts with respect to the sample width center. This graph is obtained as follows: values of X-ray irradiation width that the X-ray passing through the divergence slit disposed at each diffraction angle 2θ forms at the sample position is obtained by calculation under the condition in which the radius of a goniometer is set to 185 mm and divergence angle of the divergence slit is set to "1°"; and then, the values of X-ray irradiation width thus obtained are plotted in the graph. Curve A1 shows a change in the X-ray irradiation width in the right half part of the sample S shown in FIG. 12. Curve A2 shows a change in the X-ray irradiation width in the left half part of the sample S shown in FIG. 12.

As is clear from this graph, when the X-ray source F is moved from the position of X-ray incident angle θ=90° to the left side to cause the incident angle θ gradually become smaller, spread on the right side of the X-ray irradiation width and spread on the left side thereof are asymmetric. Therefore, in the case where effective divergence angle is calculated based on the sample width, it is preferable to perform calculation separately for the right and left sides of the sample width so as to obtain a more correct effective divergence angle.

FIG. 14 shows a graph appearing how the diffracted X-ray intensity changes as varies of diffraction angle with the sample width 2A used as a parameter. Here, the part β1 of effective divergence angle and the part β2 thereof are calculated according to the above expressions (4) and (5), with respect to a plurality of different sample width 2A (concretely, three types of 2A=20 mm, 10 mm, and 5 mm) with the radius of a goniometer set to 185 mm and real divergence angle of the divergence slit set to "1°" in the configuration of FIG. 12. Then, expression β=β1+β2 is used to calculate effective divergence angle β, and the obtained effective divergence angle β is plotted in the graph as relative X-ray intensity (that is, intensity ratio).

The graph reveals the following.

(1) With regard to the sample having a sample width 2A=20 mm (that is, a standard-arrangement sample: curve A), relative X-ray intensity (that is, intensity ratio) becomes "1" in a range in which diffraction angle 2θ≧19.59°, and relative X-ray intensity is decreased in a range in which diffraction angle 2θ<19.59°. This means that, in the case where the sample width 2A is 20 mm, X-ray irradiation does not runs off the sample width 2A in the region in which 2θ≧19.59° to allow the relative X-ray intensity (intensity ratio) to be maintained at "1" and X-ray irradiation runs off the sample width 2A in the region in which 2θ<19.59° to cause the relative X-ray intensity (intensity ratio) to be decreased.

(2) With regard to the sample having a sample width 2A=10 mm (curve B: meaning a sample of small amount), relative X-ray intensity (intensity ratio) becomes "1" in a range in which diffraction angle 2θ≧38.7°, and relative X-ray intensity is decreased in a range in which diffraction angle 2θ<38.7°. This means that, in the case where the sample width 2A is 10 mm, X-ray irradiation does not run off the sample width 2A in the region in which 2θ≧38.7° to allow the relative X-ray intensity (intensity ratio) to be maintained at "1" and X-ray irradiation runs off the sample width 2A in the region in which 2θ<38.7° to cause the relative X-ray intensity (intensity ratio) to be decreased.

(3) With regard to the sample having a sample width 2A=5 mm (curve C: meaning a sample of much smaller amount), relative X-ray intensity (intensity ratio) becomes "1" in a range in which diffraction angle 2θ≧81.5°, and relative X-ray intensity is decreased in a range in which diffraction angle 2θ<81.5°. This means that, in the case where the sample width 2A is 5 mm, X-ray irradiation does not run off the sample width 2A in the region in which 2θ≧81.5° to allow the relative X-ray intensity (intensity ratio) to be maintained at "1" and X-ray irradiation runs off the sample width 2A in the region in which 2θ<81.5° to cause the relative X-ray intensity (intensity ratio) to be decreased.

(4) The diffraction angle at which the relative X-ray intensity starts attenuating is shifted to the high angle side as the sample width 2A becomes smaller. That is, the smaller the sample amount is, the wider the region of diffraction angle 2θ in which the relative X-ray intensity of diffracted X-ray intensity is changed on the 2θ low angle side, that is, 2θ angle region in which comparison of a diffracted X-ray profile between the cases where the sample of small amount is used and where the standard-arrangement sample is used is made difficult becomes wider on the low angle region.

(5) In the case where a diffracted X-ray peak is obtained in the 2θ region in which the relative X-ray intensity is decreased in each of the curves A, B, and C, the obtained diffracted X-ray peak is a peak obtained in a state where the relative X-ray intensity is decreased and, therefore, does not represent correct intensity. In this case, by multiplying the obtained diffracted X-ray peak by the inverse number of the slant of an intensity decreased portion of each of the curves A, B, and C, it is possible to compensate the diffracted X-ray peak to a correct state in which the relative X-ray intensity is "1". The above expression (6) means this.

Next, in the X-ray diffraction measurement method according to the present invention, it is preferable that diffracted X-ray generated from the sample be detected by the X-ray detector through a receiving slit and a monochromator. The monochromator selects X-rays out of diffracted X-rays generated by the sample in wavelength to diffract and lead them to the X-ray detector. According to this aspect of the present invention, it is possible to remove background intensity in original data before intensity compensation, thereby preventing the background intensity from being compensated together with peak intensity at the time of intensity compensation. Therefore, it is possible to obtain more correct compensation result.

Next, an X-ray diffraction apparatus according to the present invention (1) includes: an X-ray source for emitting X-ray; a sample holder for supporting a sample; a divergence slit for guiding X-ray emitted from the X-ray source to the sample by restring the divergence of the X-ray; an X-ray detector for detecting diffracted X-ray generated from the sample; an X-ray intensity calculator for calculating X-ray intensity based on an output signal of the X-ray detector; wherein (2) the divergence angle of the divergence slit is a fixed value; (3) the divergence slit is a slit that restricts X-ray irradiation width in the direction of the width of the sample supported by the sample holder; (4) the sample holder supports the sample in a longitudinally-elongated arrangement in which its sample width is smaller than a standard sample width and its sample height is the same as a standard sample height; and (5) the X-ray intensity calculator compensates X-ray intensity $I_{obs}(\theta)$ calculated based on an output of the X-ray detector based on an effective divergence angle calculated based on the sample width to thereby obtain true X-ray intensity $I_{tru}(\theta)$.

According to the apparatus of the present invention, a fixed divergence slit is used as the divergence slit, thereby simplifying the configuration and reducing cost as compared to a case where a variable divergence slit is used. Further, measurement is performed with the sample arranged in a longitudinally-elongated manner (see FIG. 8B), so that diffracted X-ray with a higher intensity can be obtained in 2θ high angle region as compared to a case where the sample is arranged in a laterally-elongated manner (see FIG. 8A) even if the amount of the sample is small, thereby obtaining correct diffraction data in a short period of time.

When measurement is performed on the sample arranged in the longitudinally-elongated arrangement, X-ray irradiation width runs off the sample width not only in a low 2θ-angle region (e.g., 20° or less) but also in a middle 2θ-angle region (e.g., about 60°). Therefore, the relative X-ray intensity (intensity ratio) even in the 2θ middle angle regions may differ from that of the standard-arrangement sample. As a result, even if qualitative analysis is performed by comparing a diffraction profile calculated by measurement performed for the sample of longitudinally-elongated arrangement with standard data (e.g., ICDD card data) previously calculated with respect to the standard sample, accurate results of the analysis cannot be obtained.

In order to cope with this problem, in the present invention, X-ray intensity calculated based on the output of the X-ray detector is corrected based on an effective divergence angle calculated from the sample width. Therefore, a decrease of the relative X-ray intensity (intensity ratio) in the low 2θ-angle region, which is exhibited in the sample S arranged in a longitudinally-elongated manner, is compensated to maintain the relative X-ray intensity at a constant value. Thus, when qualitative analysis is performed by comparing a diffraction profile of the sample having a small sample width with a standard diffraction profile of the sample having the standard sample width, a correct analysis result can be obtained.

Next, in the X-ray diffraction apparatus according to the present invention, (1) assuming in FIG. 11 that the sample width of the sample S is "2A", X-ray incident angle for the sample S is "θ", and radius of a goniometer is "R", it is preferable for the X-ray intensity calculator to calculate the effective divergence angle "β" according to the following expression:

$$\tan \beta = (\sin \theta)/(R/2A),$$

(2) assuming in FIG. 11 that the actual divergence angle of the divergence slit 2 is "γ" and X-ray intensity calculated based on an output of the X-ray detector 10 is $I_{obs}(\theta)$, it is preferable for the X-ray intensity calculator to calculate true X-ray intensity $I_{tru}(\theta)$ according to the following expression:

$$I_{tru}(\theta) = (\gamma/\beta) I_{obs}(\theta)$$

Further, in the X-ray diffraction apparatus according to the present invention, (1) assuming in FIG. 12 that the sample width of the sample S is "2A", X-ray incident angle for the sample S is "θ", and radius of a goniometer is "R", it is preferable for the X-ray intensity calculator to calculate effective divergence angle part "β1" of the effective divergence angle "β" which is on the side farther away from the X-ray source F with respect to sample width center C and effective divergence angle part "β2" of the effective divergence angle "β" on the side nearer to the X-ray source F with respect to the sample width center C according to the following expressions:

$$\tan \beta 1 = (\sin \theta)/\{(R/A) - \cos \theta\}$$

$$\tan \beta 2 = (\sin \theta)/\{(R/A) + \cos \theta\}$$

(2) assuming in FIG. 12 that the actual divergence angle of the divergence slit 2 is "γ" and X-ray intensity calculated based on an output of the X-ray detector 10 is $I_{obs}(\theta)$, it is preferable for the X-ray intensity calculator to calculate true X-ray intensity $I_{tru}(\theta)$ according to the following expression:

$$I_{tru}(\theta) = \{\gamma/(\beta 1 + \beta 2)\} \times I_{obs}(\theta).$$

In this invention aspect based on FIG. 12, the effective divergence angle in the invention aspect based on FIG. 11 is analyzed with a higher precision, so that compensation of relative X-ray intensity (intensity ratio) is performed more precisely.

Next, in the X-ray diffraction apparatus according to the present invention, it is preferable that the X-ray intensity calculator calculates X-ray intensity $I_{obs}(\theta)$ by accumulating output signals of the X-ray detector during a predetermined sampling time, further calculates true X-ray intensity $I_{tru}(\theta)$ from X-ray intensity $I_{obs}(\theta)$ every sampling time, and store the obtained true X-ray intensity $I_{tru}(\theta)$ According to this aspect of the present invention, the true X-ray intensity $I_{tru}(\theta)$ is not treated as compensation result but as raw data representing measurement result itself. The true X-ray intensity $I_{tru}(\theta)$ can be input to an image data calculation circuit immediately so as to be displayed on the screen of a display or printed by a printer. Further, the true X-ray intensity $I_{tru}(\theta)$ is stored in a predetermined storage area either of an internal storage device within a computer or an external storage apparatus, not as compensation result but as raw data representing measurement result itself.

Alternatively, the X-ray intensity $I_{obs}(\theta)$ may directly be stored without being subjected to the compensation processing. In this case, the X-ray intensity $I_{obs}(\theta)$ may be compensated to the true X-ray intensity $I_{tru}(\theta)$ at the data processing occurred later and then stored.

Next, it is preferable that the X-ray diffraction apparatus according to the present invention comprise: a receiving slit provided between the sample holder and the X-ray detector; and a monochromator provided between the receiving slit and the X-ray detector. In this case, the monochromator selects X-rays out of diffracted X-rays generated by the sample in wavelength to diffract and lead them to the X-ray detector. According to this aspect of the present invention, it is possible to remove background intensity in original data before intensity compensation, thereby preventing the background intensity from being compensated together with peak intensity at the time of intensity compensation. Therefore, it is possible to obtain more correct compensation result.

BRIEF DESCRIPTION OF THE DRAWINGS

FIGS. 6A and 6B are views showing an example of measurement using a standard sample holder, in which FIG. 6A shows a plan configuration and FIG. 6B shows a cross-sectional configuration taken along the $Z_6$-$Z_6$ line of FIG. 6A;

FIGS. 9A and 9B are views showing an embodiment of an X-ray diffraction measurement method according to the present invention, in which FIG. 9A shows a plan configuration and FIG. 9B shows a cross-sectional configuration taken along the $Z_{10}$-$Z_{10}$ line of FIG. 9A;

DETAILED DESCRIPTION OF THE PREFERRED EMBODIMENTS

Figure 1:
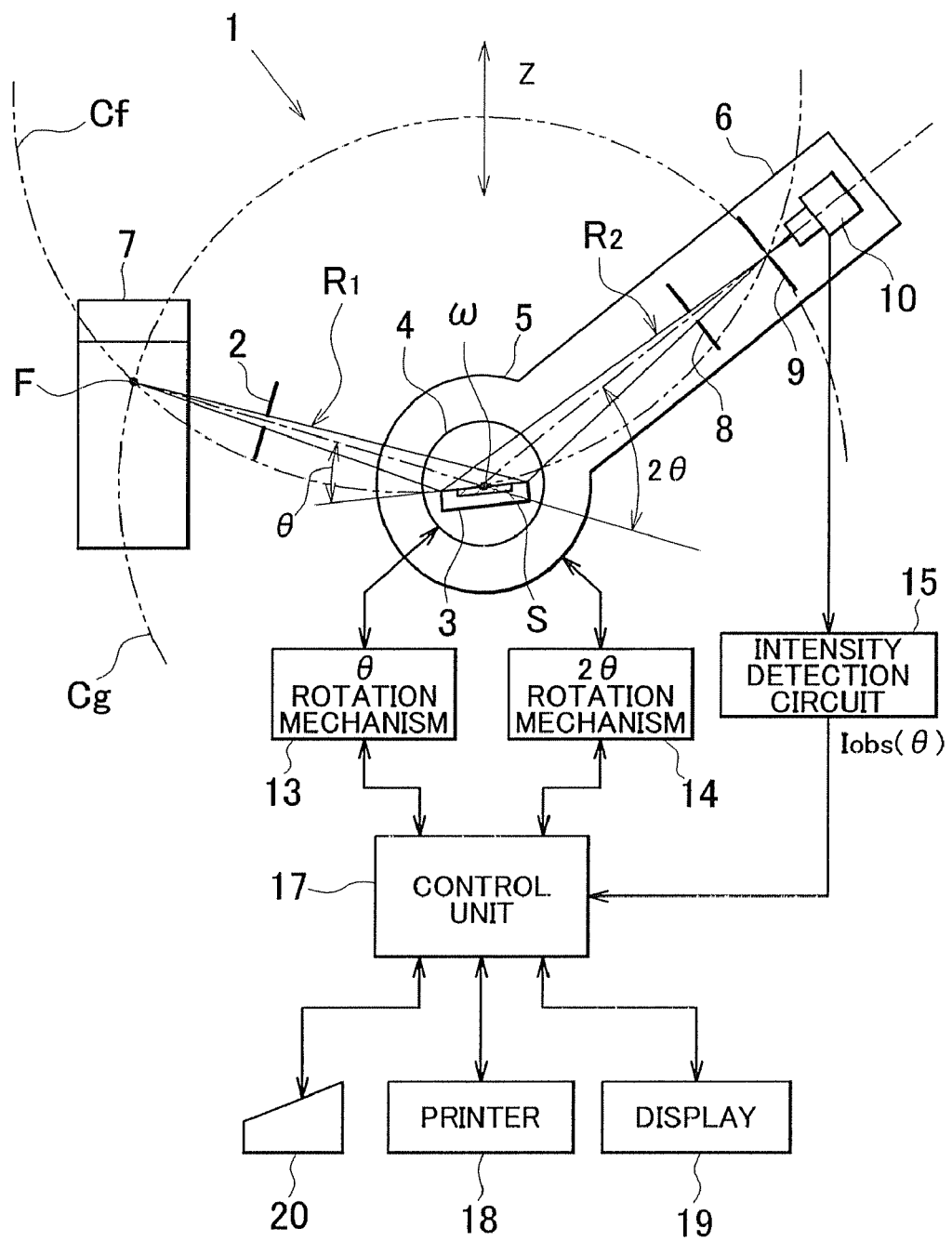
FIG. 1 is a view showing an embodiment of an X-ray diffraction apparatus for embodying an X-ray diffraction measurement method according to the present invention.

An X-ray diffraction measurement method and an X-ray diffraction apparatus according to the present invention will be described based on a preferred embodiment. It should be noted that the present invention is not limited to the following embodiment. Although the following description is made with the accompanying drawings, there is a case where components in the drawings may be shown at a different scale from actual ones for easy understanding of their feature points.

FIG. 1 shows an embodiment of an X-ray diffraction apparatus according to the present invention. FIG. 1 is a front view, in which left-right direction is horizontal direction and up-down direction is vertical direction. An X-ray diffraction apparatus 1 shown in FIG. 1 has an X-ray source F for generating X-ray, a divergence slit 2 for restricting divergence of X-ray, a θ-rotation table 4 for supporting a sample holder 3, a 2θ-rotation table 5 coaxially arranged with the θ-rotation table 4, and a detector arm 6 extending from the 2θ-rotation table 5.

The X-ray source F is constituted by a filament for generating thermal electron by current application and a target disposed opposite to the filament. More specifically, the region at which the thermal electron collides with the target on the outer circumferential surface thereof corresponds to an X-ray focus, and this X-ray focus corresponds to the X-ray source F. The surface of the target forming the X-ray source F is made of, for example, Cu (copper). The X-ray source F is provided within an X-ray tube 7 inside of which is under vacuum. X-ray emitted from the X-ray source F travels downward at an angle of about 6° relative to the horizontal direction and taken out of the X-ray tube 7. The X-ray source F and the divergence slit 2 are immovably fixed. A sample S is filled into a predetermined position of the sample holder 3. The divergence slit 2 restricts the divergence of X-ray so as to allow X-ray generated in the X-ray source F to be incident on the sample S.

A scattering slit 8, a receiving slit 9, and an X-ray detector 10 are fixed on the detector arm 6. A θ-rotation mechanism 13 is coupled to the θ-rotation table 4. A 2θ-rotation mechanism 14 is coupled to the 2θ-rotation table 5. The θ-rotation mechanism 13 and the 2θ-rotation mechanism 14 are mechanisms for rotating the θ-rotation table 4 and the 2θ-rotation table 5 with high angular accuracy, respectively. The above mechanisms may use a power transmission system including, for example, a worm and worm wheel to transmit rotation of an electric motor such as a servomotor or a pulse motor to the respective rotation tables 4 and 5.

The scattering slit 8 prevents scattered X-ray generated from a region other than the sample (for example, scattered X-ray generated due to air scattering) from being received by the X-ray detector 10. The receiving slit 9 is disposed at a focal point of X-ray diffracted by the sample S and prevents X-ray other than the focused X-ray from being received by the X-ray detector 10. The X-ray detector 10 is, for example, a zero-dimensional X-ray detector. The zero-dimensional X-ray detector detects X-ray received at a predetermined area in a dotted manner without determining its reception position and is constituted by using, for example, an SC (Scintillation Counter) The X-ray detector 10 outputs a signal corresponding to the amount of the received X-ray. Based on the output signal, an intensity detection circuit 15 calculates the X-ray intensity. The intensity detection circuit 15 may be incorporated apparently in the X-ray detector 10.

The zero-dimensional X-ray detector basically indicates an X-ray detector other than a one-dimensional X-ray detector, such as a PSPC (that is, Position Sensitive Proportional Counter) that detects X-ray in a linear region, a two-dimensional X-ray detector, such as an X-ray detector using a planar X-ray phosphor that detects X-ray in a planar region. If the one-dimensional X-ray detector and the two-dimensional X-ray detector are used as the zero-dimensional X-ray detector, the one-dimensional X-ray detector and the two-dimensional X-ray detector are assumed to be included in the zero-dimensional X-ray detector.

The incident angle of X-ray R1 which is emitted from the X-ray source F and is incident on the sample S through the divergence slit 2 is assumed to be "$\theta$". The diffraction angle of diffracted X-ray R2 detected by the X-ray detector 10 is assumed to be "$2\theta$". When the $\theta$-rotation table 4 is rotated by the $\theta$-rotation mechanism 13, X-ray incident angle $\theta$ correspondingly varies. This rotation of the $\theta$-rotation table 4 is referred to as "$\theta$-rotation". When the $2\theta$-rotation table 5 is rotated by the $2\theta$-rotation mechanism 14, the diffraction angle $2\theta$ correspondingly varies. This rotation of the $2\theta$-rotation table 5 is referred to as "$2\theta$-rotation". The $2\theta$-rotation table 5 is rotated at an angular speed double that of the $\theta$-rotation of the $\theta$-rotation table 4 and in the same direction as that of the $\theta$-rotation of the $\theta$-rotation table 4.

In order to achieve the $\theta$-rotation, it is sufficient for the X-ray source F and sample S to be rotated relative to each other. Thus, a configuration may be adopted in which the sample S is fixedly disposed and the X-ray source F is driven to rotate in a manner of the $\theta$-rotation. In this case, the $2\theta$-rotation table 5 is rotated at the same angular speed as that of the $\theta$-rotation of the X-ray source F and in the opposite direction to that of the $\theta$-rotation of the X-ray source F, so that the X-ray detector 10 always keep the diffraction angle $2\theta$ that is double angle of the X-ray incident angle $\theta$.

An angle measuring mechanism constituted by the $\theta$-rotation table 4, $\theta$-rotation mechanism 13, $2\theta$-rotation table 5, $2\theta$-rotation mechanism 14, and detection arm 6 is a goniometer. An optical system from the X-ray source F to the X-ray detector 10 including the goniometer, more specifically, an optical system including the X-ray source F, divergence slit 2, sample S, scattering slit 8, receiving slit 9, X-ray detector 10, and goniometer is an X-ray optical system. The present embodiment employs an X-ray optical system in which a plane depicted by turning of X-ray optical axes (that is, center lines of X-ray R1 and X-ray R2) during $\theta$-rotation of X-ray source F and $2\theta$-rotation of X-ray detector 10 is included in the vertical plane. This type of X-ray optical system can be called "vertical X-ray optical system". Instead the present embodiment may employ an X-ray optical system in which a plane depicted by turning of X-ray optical axes during $\theta$-rotation of X-ray source F and $2\theta$-rotation of X-ray detector 10 is included in the horizontal plane. This type of X-ray optical system can be called "horizontal X-ray optical system".

In the present embodiment the X-ray optical system is based on the principle of a focusing method, in which the X-ray source F and the receiving slit 9 are always present on a goniometer circle $C_g$ having a center axis $\omega$ passing along the surface of the sample S and extending perpendicular to the plane of FIG. 1 as X-ray incident angle $\theta$ and X-ray diffraction angle $2\theta$ vary. Further, three points of the X-ray source F, the sample S, and the receiving slit 9 are present on a focusing circle $C_f$ as X-ray incident angle $\theta$ and X-ray diffraction angle $2\theta$ vary.

X-ray intensity signal $I_{obs}(\theta)$ output from the intensity detection circuit 15 is input to a control unit 17. The control unit 17 is constituted by a computer including a CPU (Central Processing Unit), a memory, and the like. The $\theta$-rotation mechanism 13 and $2\theta$-rotation mechanism 14 are connected to the input/output section of the control unit 17. Further, an input device 2 such as a keyboard or mouse is connected to the input/output section of the control unit 17. In addition, a printer 18 and a display 19 each serving as an output device are connected to the control unit 17.

Figure 2:
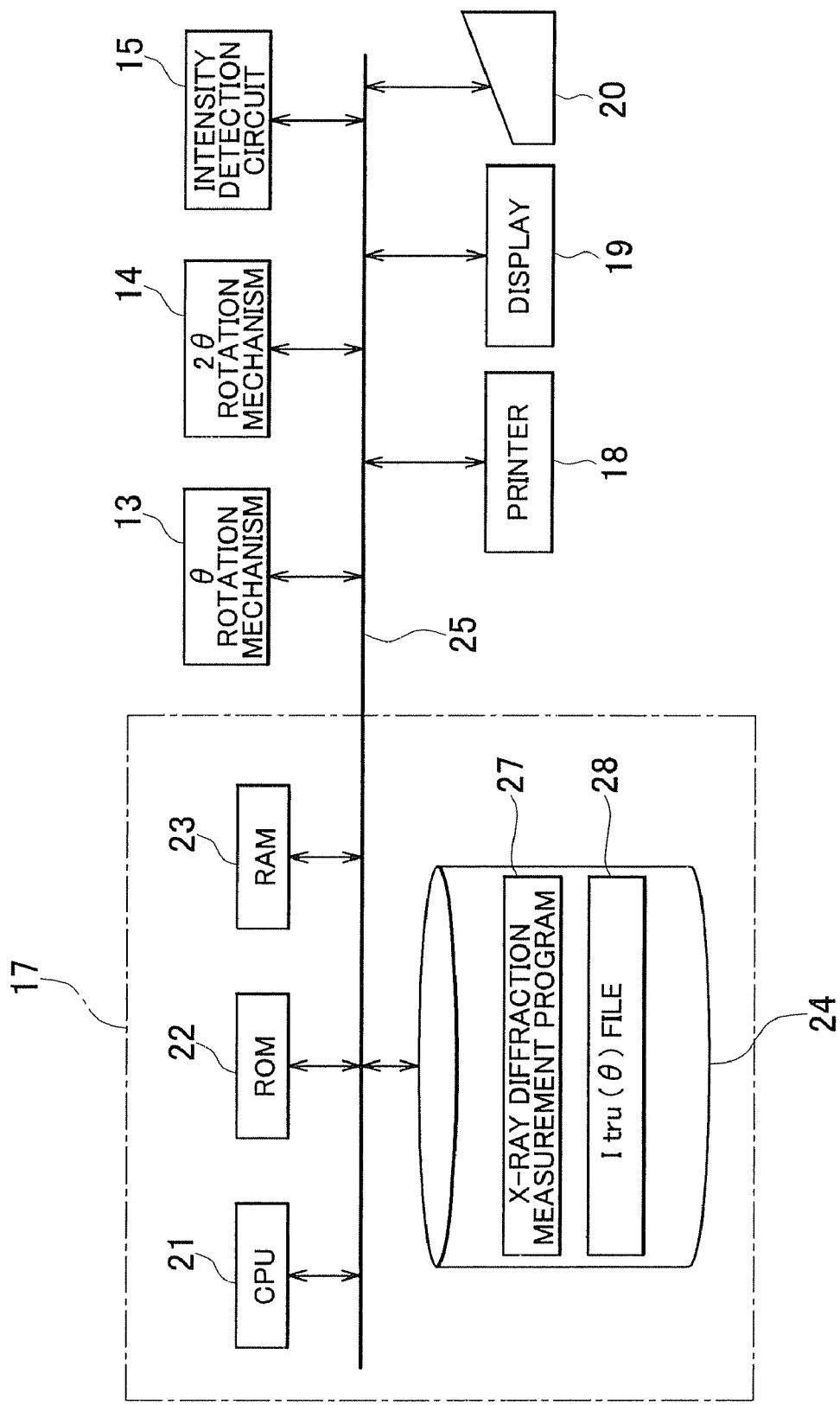
FIG. 2 is a block diagram showing an electrical control system in the configuration of FIG. 1.

As shown in FIG. 2, the control unit 17 includes a CPU (Central Processing Unit) 21, a ROM (Read Only Memory) 22, a RAM (Random Access Memory) 23, a memory 24, and a bus 25 connecting the above-mentioned components. The memory 24 may be constituted by an appropriate storage medium such as a mechanical memory (for example, hard disk, CD (Compact Disk), MO (Magneto-optic)) or semiconductor memory. The CPU 21 performs calculation and control according to a program stored in the memory 24. The ROM 22 stores basic data or basic operating system. The RAM 23 functions as a potential file for temporarily storing various data.

The $\theta$-rotation mechanism 13, the $2\theta$-rotation mechanism 14, the input device 20, the printer 18, the display 19, and the intensity detection circuit 15 shown in FIG. 1 are connected to the control unit 17 through the bus 25 in FIG. 2. A file 27 storing a program software for executing X-ray diffraction measurement and a file 28 for storing diffracted X-ray intensity data $I_{tru}(\theta)$ to be described later are placed in the memory 24.

In FIG. 1, solar slits may be disposed between the X-ray source F and the divergence slit 2 and between the scattering slit 8 and the receiving slit 9 as occasion demands. These solar slits restrict the spread of X-ray in the vertical direction (that is, Z-direction) to prevent the resolution of a diffracted X-ray peak from being deteriorated. Further, a monochromator may be disposed between the receiving slit 9 and the X-ray detector 10 according to need. The monochromator can remove unnecessary K$\beta$-rays and can cut continuous X-ray or fluorescence X-ray that exerts an adverse affect on detection of an extremely small peak.

As shown in FIGS. 3A to 3F, the sample holder 3 is formed by forming an opening 11 for filling the sample in a metal plate having a thickness of several mm, such as an AL (aluminum) plate. Although the opening 11 is a through hole in the present embodiment, it may be formed in a bottomed concave shape. In the present embodiment, six types of sample holder 3 having openings 11 with different widths of 20 mm (FIG. 3A), 12 mm (FIG. 3B), 8 mm (FIG. 3C), 4 mm (FIG. 3D), 2 mm (FIG. 3E), and 1 mm (FIG. 3F) are prepared. The heights of the above openings 11 are set to the same value, which is 20 mm. When the sample is filled into the opening 11, the width of the opening 11 means the sample width. Hereinafter, the opening 11 is sometimes referred to as "sample area".

Figure 3A:
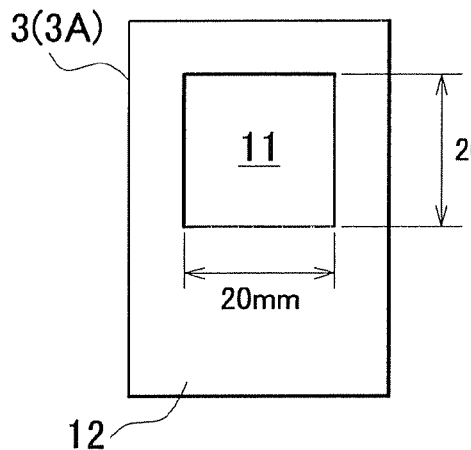
FIGS. 3A, 3B, 3C, 3D, 3E, and 3F are plan views each showing an example of a sample holder used in the X-ray optical system shown in FIG. 1.
Figure 3D:
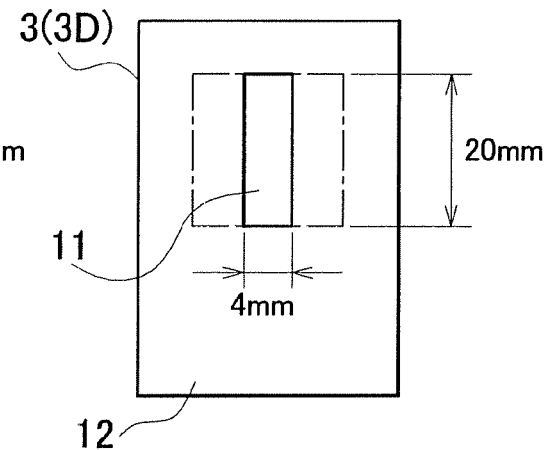
Figure 3B:
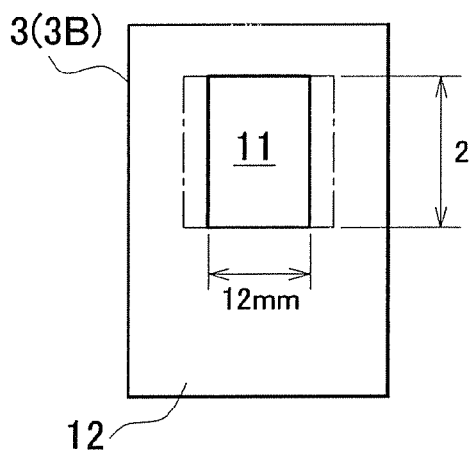
Figure 3E:
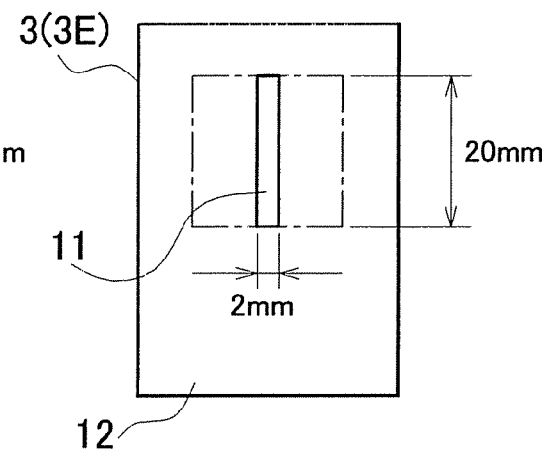
Figure 3C:
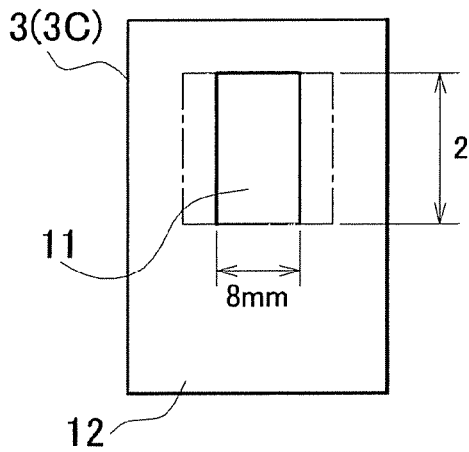
Figure 3F:
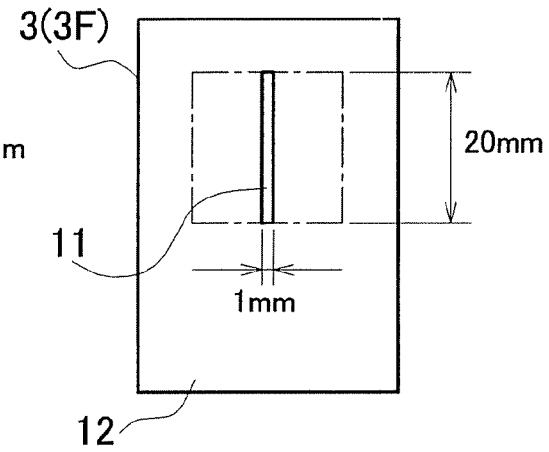

The sample holder 3A of FIG. 3A is a standard sample holder that is used in the case where the amount of the sample to be measured is sufficient and has an opening 11 with the largest capacity (hereinafter, sometimes referred to as "area", when viewed in a planar manner). The sample area (that is, opening) 11 of the standard sample holder 3A is an area corresponding to the standard data (for example, ICDD card) commonly used in the field of qualitative analysis of X-ray diffraction measurement. The sample holders 3B to 3F shown in FIGS. 3B to 3F are sample holders used in the case where the available sample is limited to a small amount.

In each of the sample holders 3B to 3F, the width of the opening 11 is smaller than that of the opening 11 of the standard sample holder 3A, and the amount of the sample that can be filled into the opening 11 correspondingly becomes smaller. In the actual measurement, a sample holder having an opening 11 with the optimum capacity is selected in accordance with the amount of the available sample. Although the detail is described later, diffracted X-ray intensity compensation processing differs depending on which one of the sample holders 3A to 3F is used.

Figure 4:
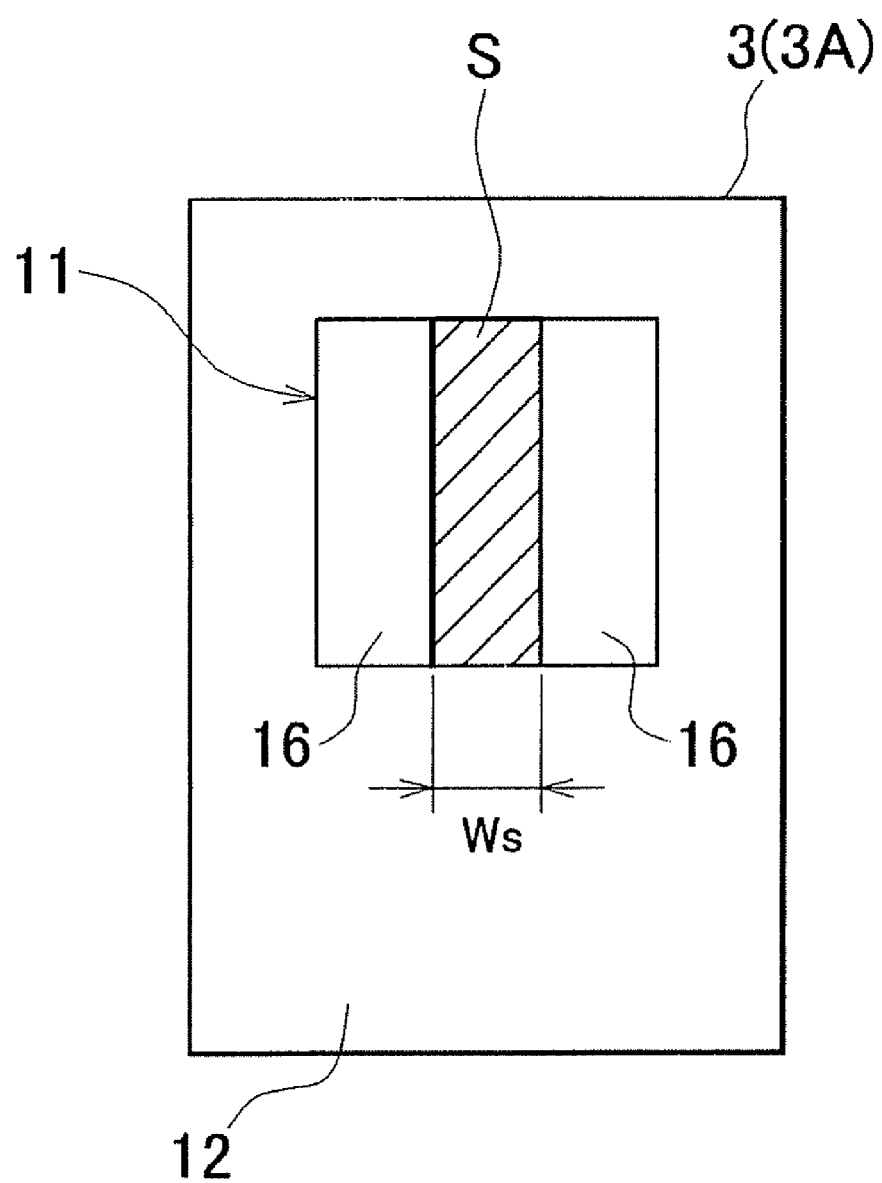
FIG. 4 is a plan view showing another example of the sample holder used in the X-ray optical system shown in FIG. 1.

The diffraction measurement can be performed without the use of the sample holders 3B to 3F (FIGS. 3B to 3F) having a sample width smaller than a standard size (20 mm). In this case, as shown in FIG. 4, only the standard sample holder 3A is prepared, non-crystalline solids (for example, glass body) 16 each having an adequate width are attached to the left and right ends of the opening 11 of the standard sample holder 3A, and sample S is filled into the narrowed area between the non-crystalline solids 16.

In FIGS. 3A to 3F and FIG. 4, each of the sample holder 3 is attached to a predetermined portion of the θ-rotation table 4 of FIG. 1 at its side portion 12 on the side farther away from the opening 11 and thereby disposed in a predetermined location in the X-ray optical system. At this time, in each of the sample holders 3B to 3F (FIGS. 3B to 3F), the sample filled into the opening 11 assumes the longitudinally-elongated arrangement relative to the X-ray source F as shown in FIG. 8B.

Next, operation of the X-ray diffraction apparatus having the configuration described above will be described with reference to a flowchart of FIG. 5. Since processing is different between the cases where the amount of the sample is large and where the amount of the sample is small, description is made separately therefore.

(Measurement in the Case where Sample Amount is Large)

Figure 6A:
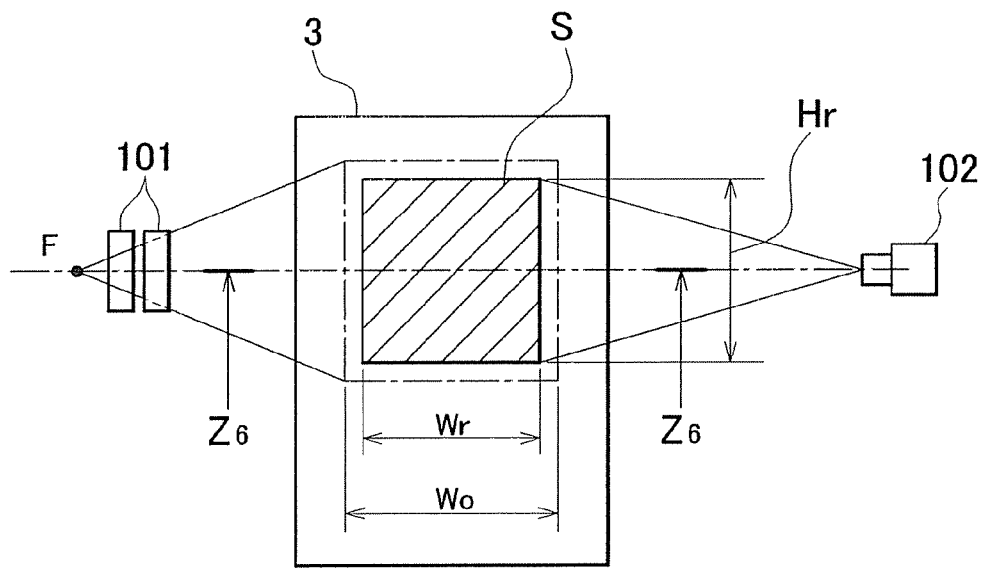
Figure 6B:
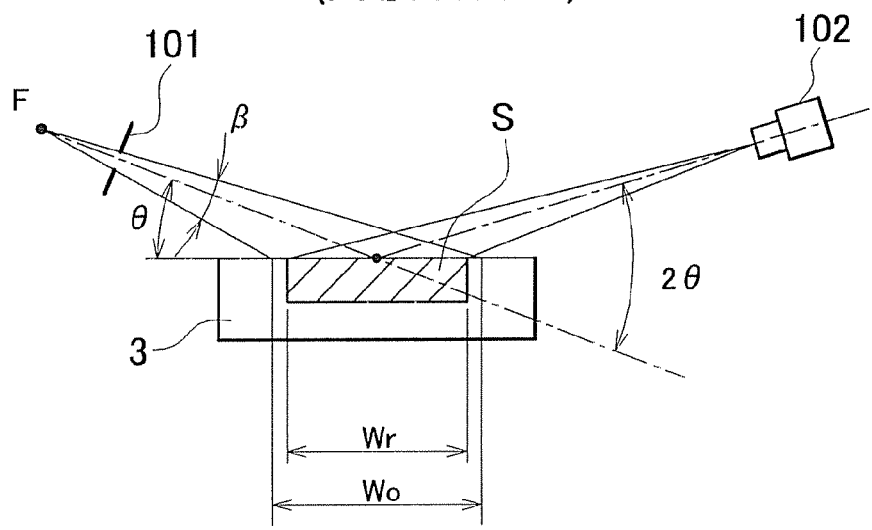
Figure 7C:
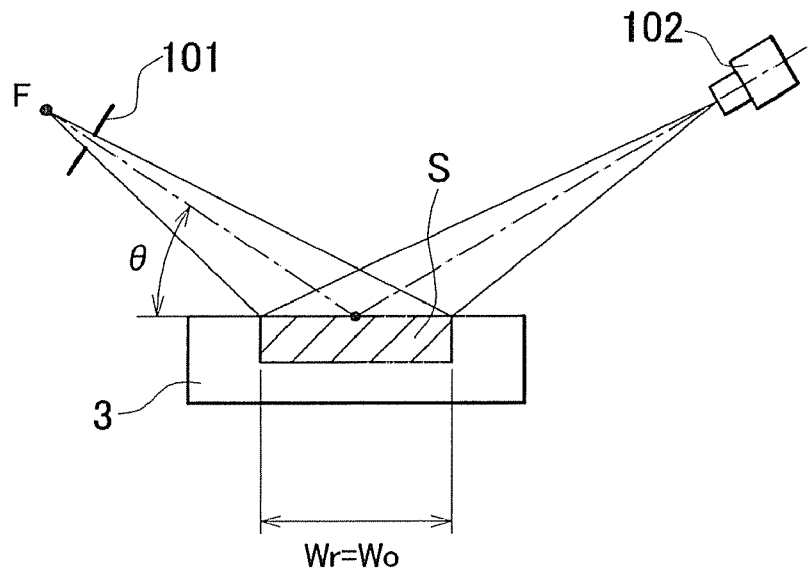
FIGS. 7C and 7D are views showing the same measurement example as FIG. 6B at a different moment of time in measurement.
Figure 7D:
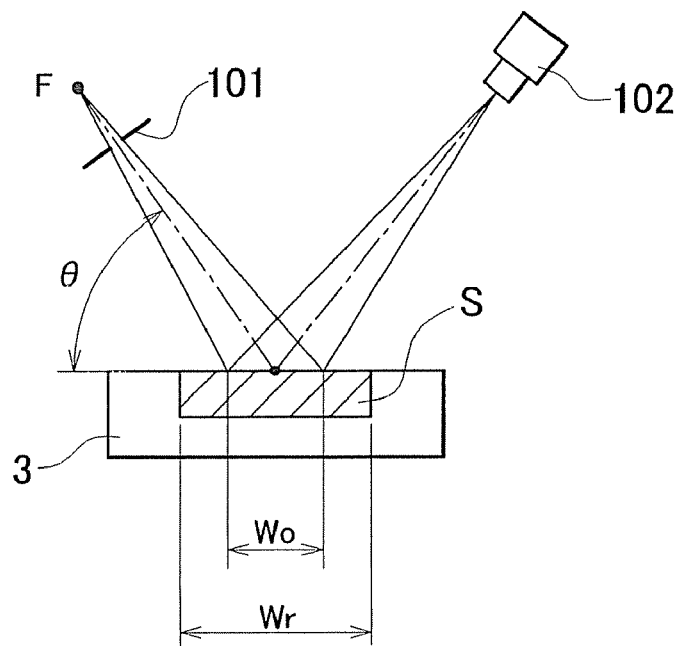

In the case where the amount of the sample to be measured is sufficient, an operator selects the sample holder 3A of FIG. 3A having the opening 11 with the standard sample area and injects the sample into the opening 11 and then attaches the sample holder 3A to a predetermined portion of the θ-rotation table 4. As a result, the sample S is disposed on the X-ray irradiation path extending from the X-ray source F to X-ray detector 10 as shown in FIGS. 6A and 6B.

Figure 5:
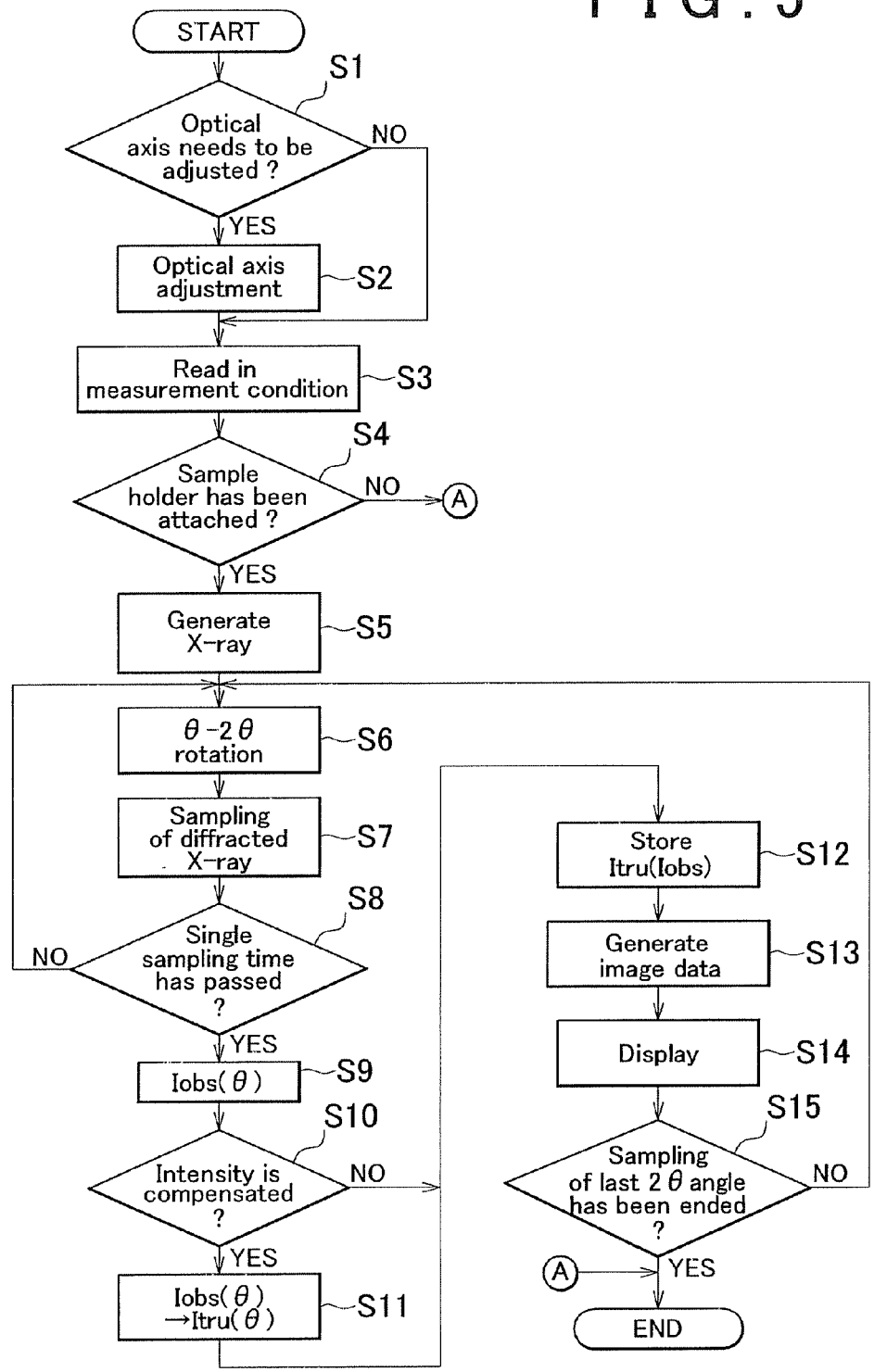
FIG. 5 is a flowchart showing the flow of control performed by the apparatus of FIG. 1.

Then, in steps S1 to S2 of FIG. 5, adjustment of the optical axis of the X-ray optical system of FIG. 1 is performed according to need. Then, in step S3, a measurement condition stored in a predetermined area in the memory 24 of FIG. 2 is read in. This measurement condition means various conditions under which the measurement using the X-ray optical system of FIG. 1 is performed and includes information which one of the sample holders 3A to 3F (FIGS. 3A to 3F) is used as the sample holder 3.

The information concerning the sample holder 3 is previously input by the operator through the input device 20 of FIG. 1. As the input method, an alternative selection method is preferably used to select any one of the six sample holders 3. When the non-crystalline solids 16 are used to narrow the sample area as described in connection with FIG. 4, it is preferable for the operator to designate sample width Ws by entering a numerical value.

Another input method can be achieved by unique marks assigned to the respective sample holders 3 and a mark read sensor provided at an appropriate position of the θ-rotation table 4. In this case, when the sample holder 4 is attached to the θ-rotation table 4, the mark read sensor automatically reads the width (that is, sample width) of the opening 11 of the attached sample holder 3.

Since the measurement to be described hereinafter is measurement performed in the case where the amount of the sample to be measured is sufficient, the operator selects the standard sample holder 3A of FIG. 3A and fill the sample into the opening 11 of the holder 3A and then inputs an instruction indicating that the standard sample holder 3A is selected through the input device 20 of FIG. 1.

After confirmation of attachment of the sample holder 3 in step S4, irradiation of X-ray including CuKα-rays from the X-ray source F is started in step S5, and θ-rotation of the θ-rotation table 4 and 2θ-rotation of the 2θ-rotation table 5 are started in step S6. While X-ray incident angle θ and diffracted X-ray detection angle 2θ are increased from their initial value respectively, diffracted X-ray is generated from the sample S when the Bragg's diffraction condition:

$$2d \sin \theta = n\lambda$$

is satisfied between X-ray incident angle θ and sample S. Note that in the above formula, "d" is lattice spacing, "λ" is wavelength of X-ray, and "n" is reflection order.

The generated diffracted X-ray is received by the X-ray detector 10 and, at this time, a detection signal is output from the X-ray detector 10. The output signal is transmitted to the intensity detection circuit 15, and the intensity detection circuit 15 calculates the X-ray intensity based on the output signal. The calculated X-ray intensity signal $I_{obs}(\theta)$ is transmitted to the control unit 17. The control unit 17 performs accumulation of the X-ray intensity signal every predetermined sampling time in steps S7 and S8 and determines the accumulated X-ray intensity as X-ray intensity $I_{obs}(\theta)$ of corresponding diffraction angle 2θ (step S9). In the present specification, diffracted X-ray intensity I(2θ) having a variable of diffraction angle 2θ is assumed to have a variable of X-ray incident angle θ for the sake of simplicity, to be expressed as I(θ).

In the manner as described above, X-ray intensity $I_{obs}(\theta)$ corresponding to each diffraction angle 2θ is obtained. In place of the control unit 17, the intensity detection circuit 15 may perform the above-mentioned calculation of X-ray intensity $I_{obs}(\theta)$.

As a sampling method, a continuous sampling method, as well as a stepwise sampling method can be used. The continuous sampling method is a method that continuously rotates the X-ray detector 10 in a manner of a 2θ-rotation to update 2θ-angle at predetermined time intervals so as to capture the diffracted X-ray. The step sampling method is a method that intermittently rotates the X-ray detector 10 in a manner of a 2θ-rotation at predetermined time intervals to update 2θ-angle so as to capture the diffracted X-ray at respective stop position in the 2θ-rotation. Either method can be employed in the present embodiment.

Then, in step S10, it is determined whether the diffracted X-ray intensity is compensated or not. This compensation should be performed to compensate decrease of the relative X-ray intensity (intensity ratio) of the diffracted X-ray at 2θ low angle region as shown in curve B or C of FIG. 14, which occurs when the amount of the sample is small, that is, measurement is performed using sample holders 3B to 3F (FIGS. 3B to 3F) other than the standard sample holder 3A of FIG. 3A. Since the measurement to be described here is measurement performed in the case where the amount of the sample to be measured is sufficient, that is, measurement using the standard sample holder 3A of FIG. 3A, and it has been confirmed in step S3 that the operator has selected the standard sample holder 3A, the CPU determines "No" in step S10 and advances to step S12.

X-ray intensity $I_{obs}(\theta)$ measured in steps S7 to S9 is sequentially stored in a predetermined area in the RAM 23 or the memory 24 of FIG. 2 in step S12 while the measurement is performed. Then, the CPU generates image data, such as color image data of R, G, B in step S13. The image data may be data for one-dimensional image, for two-dimensional image, or for three-dimensional image. The "one-dimensional image" is an image representing information by a line depicted in a plane. The "two-dimensional image" is an image representing information by a surface depicted in a plane. The "three-dimensional image" is an image representing information by a perspective expression depicted in a plane.

Figure 15:
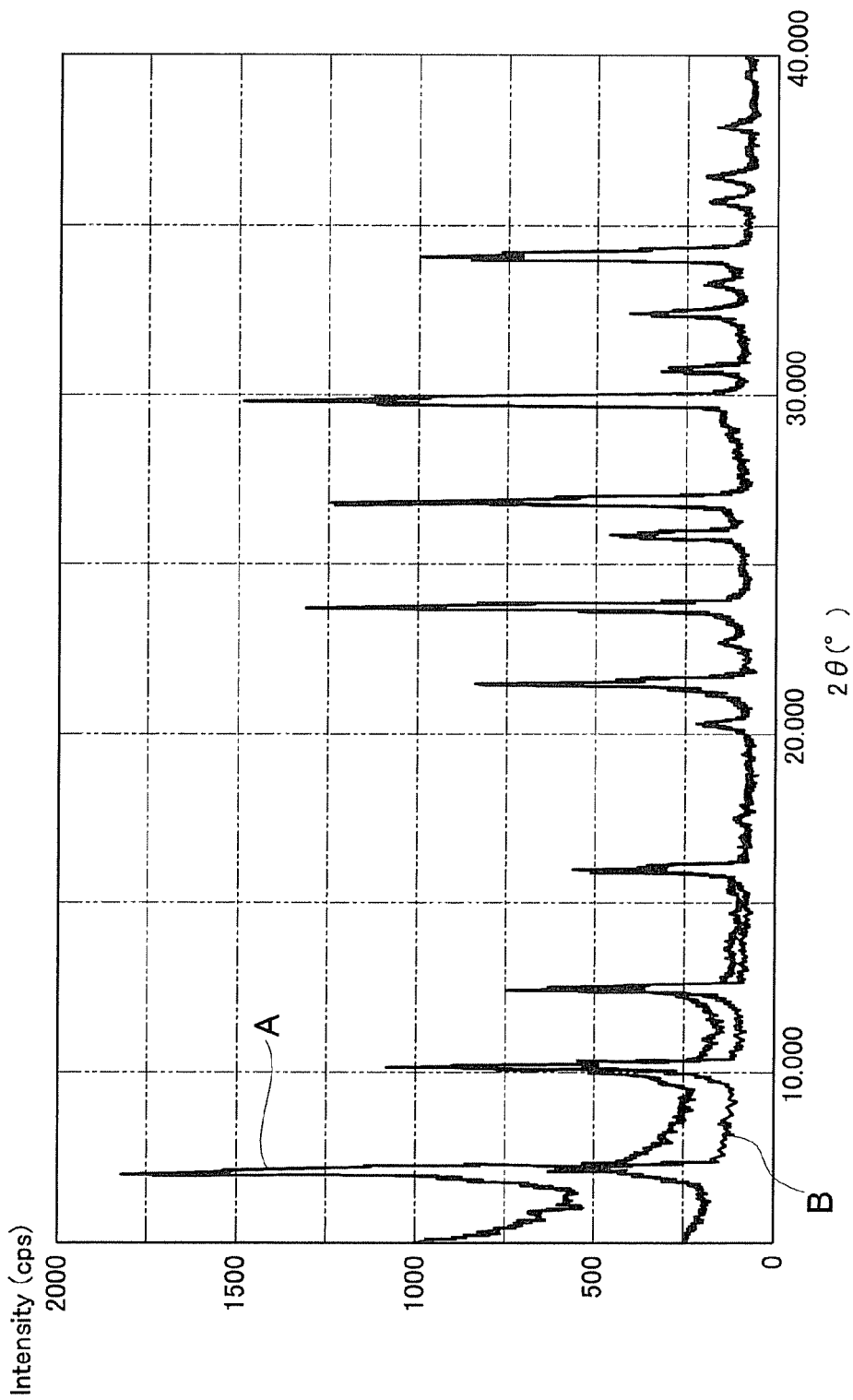
FIG. 15 is output data showing a result of an experiment using a method according to the present invention.

The generated image data is transmitted to an image controller in the display 19 of FIG. 2 in step S14 and displayed on the screen as an image. For example, as shown in FIG. 15, the generated image data is displayed as diffracted X-ray profile A or diffracted X-ray profile B on a plane coordinate system where the horizontal axis denotes diffraction angle 2θ and vertical axis denotes diffracted X-ray intensity. The graph shown in FIG. 15 is one-dimensional image. The display of the generated image data can be performed before the end of the measurement, that is, before the θ-rotation and 2θ-rotation have reached their final angle values. In this case, the diffracted X-ray profile A and the like are sequentially displayed from a low 2θ-angle side.

The CPU creates print data for the printer 18 based on $I_{obs}(\theta)$ obtained by the measurement and sends the created print data to a drive control circuit of the printer 18. As a result, $I_{obs}(\theta)$ can be printed on a paper or the like. It is thought that there is little need to start the printing of the print data during the θ-2θ measurement, so that the print data may be created after the completion of the θ-2θ measurement. The processing described above is performed until the diffraction angle 2θ reaches a desirable angle. When the diffraction angle 2θ reaches the desirable angle, the CPU determines "YES" in step S15, so that the flow is ended.

(Measurement in the Case Where Sample Amount is Small)

Figure 9A:
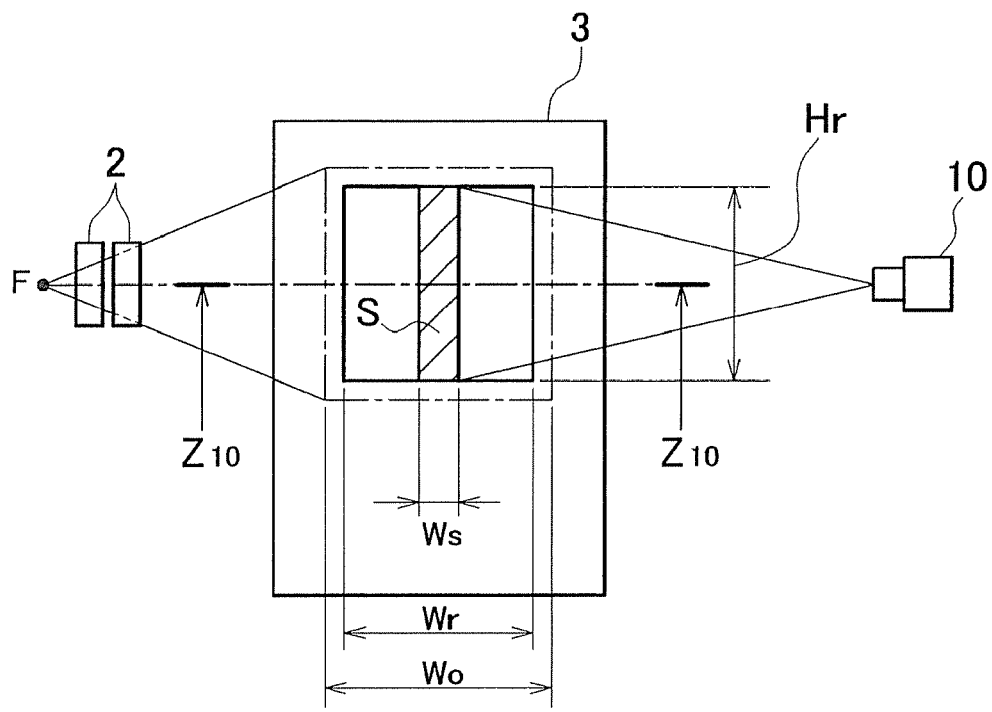
Figure 9B:
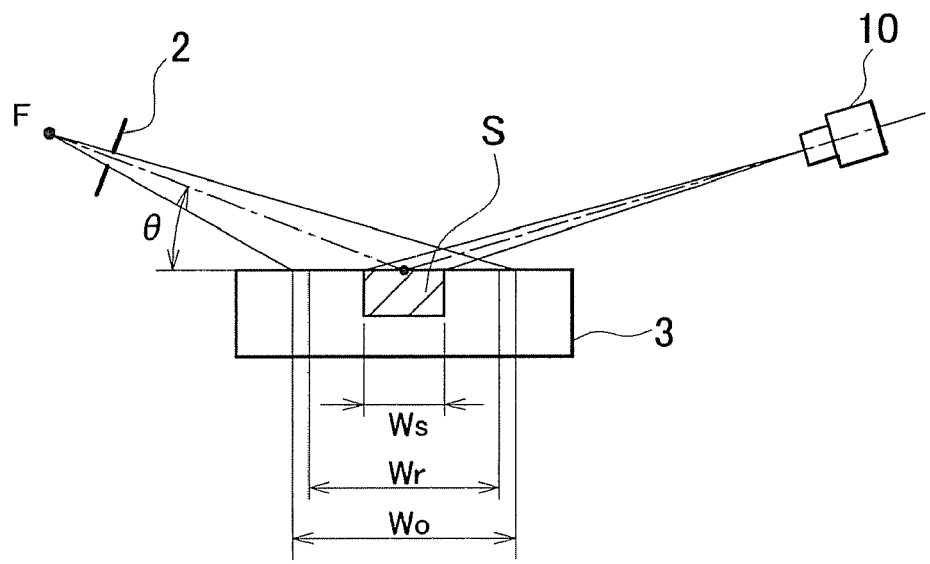
Figure 10C:
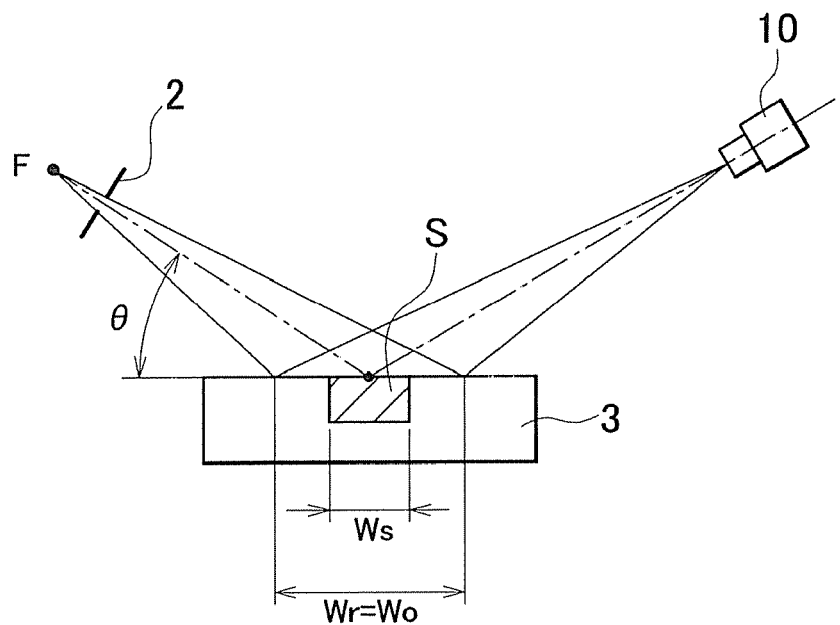
FIGS. 10C and 10D are views showing the same measurement example as FIG. 9B at a different moment of time in measurement.
Figure 10D:
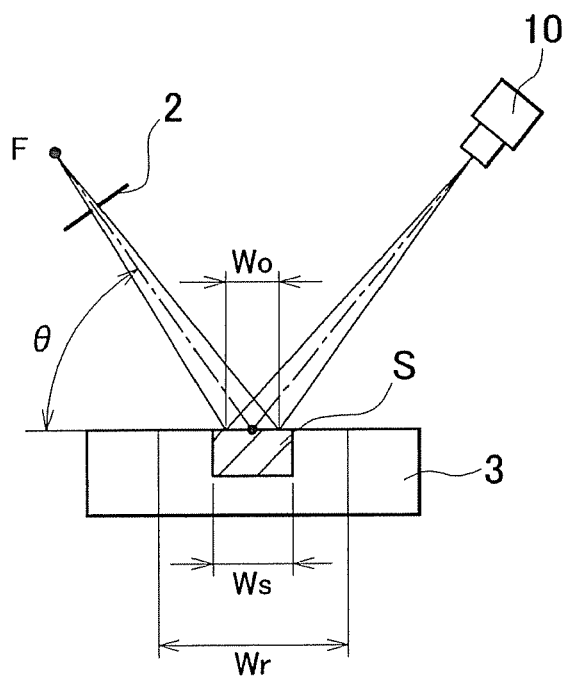

In the case where the amount of the sample to be measured is small and, therefore, it is impossible to fill the entire area of the opening 11 of the standard sample holder 3A of FIG. 3A, an operator selects one of the sample holders 3B to 3F (FIGS. 3B to 3F) having a small sample area 11 in accordance with the sample amount, fill the sample into the opening 11, and attaches the sample holder to a predetermined portion of the θ-rotation table 4. As a result, the sample S as shown in FIGS. 9A and 9B which is arranged in a longitudinally-elongated manner and has a sample width Ws smaller than the standard sample width Wr is disposed as shown in FIG. 1 on the X-ray irradiation path extending from the X-ray source F to X-ray detector 10.

First, the above-mentioned processing from steps S1 to S9 shown in FIG. 5 is performed in a manner similar to the case of the measurement for the standard-arrangement sample. Note that since an operator selects one of the sample holders 3B to 3F (FIGS. 3B to 3F) having a small sample width as a sample holder to be used before measurement, the CPU determines in step S10 that intensity compensation should be performed (that is, "YES" in step S10). Thus, the flow advances to step S11, where intensity $I_{obs}(\theta)$ which is output from the intensity detection circuit 15 while θ-2θ rotation is performed in the X-ray optical system of FIG. 1 is compensated to a true intensity $I_{tru}(\theta)$ by predetermined compensation processing every time single sampling time has passed.

Figure 8A:
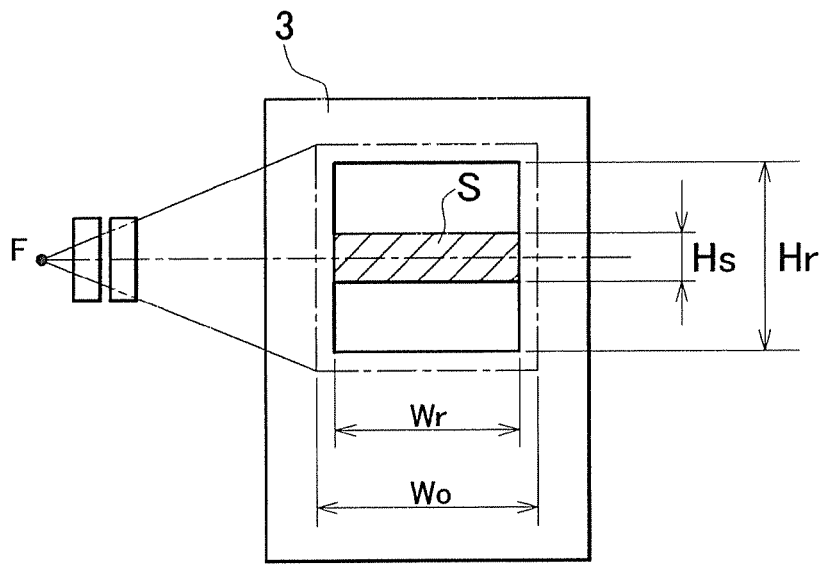
FIGS. 8A and 8B are views showing two examples how a sample of small amount is arranged.
Figure 8B:
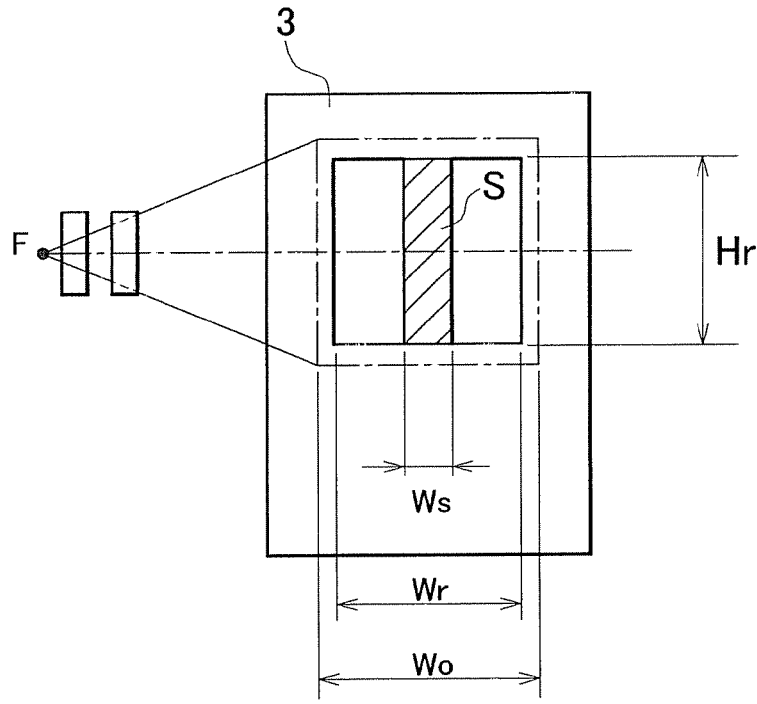
Figure 14:
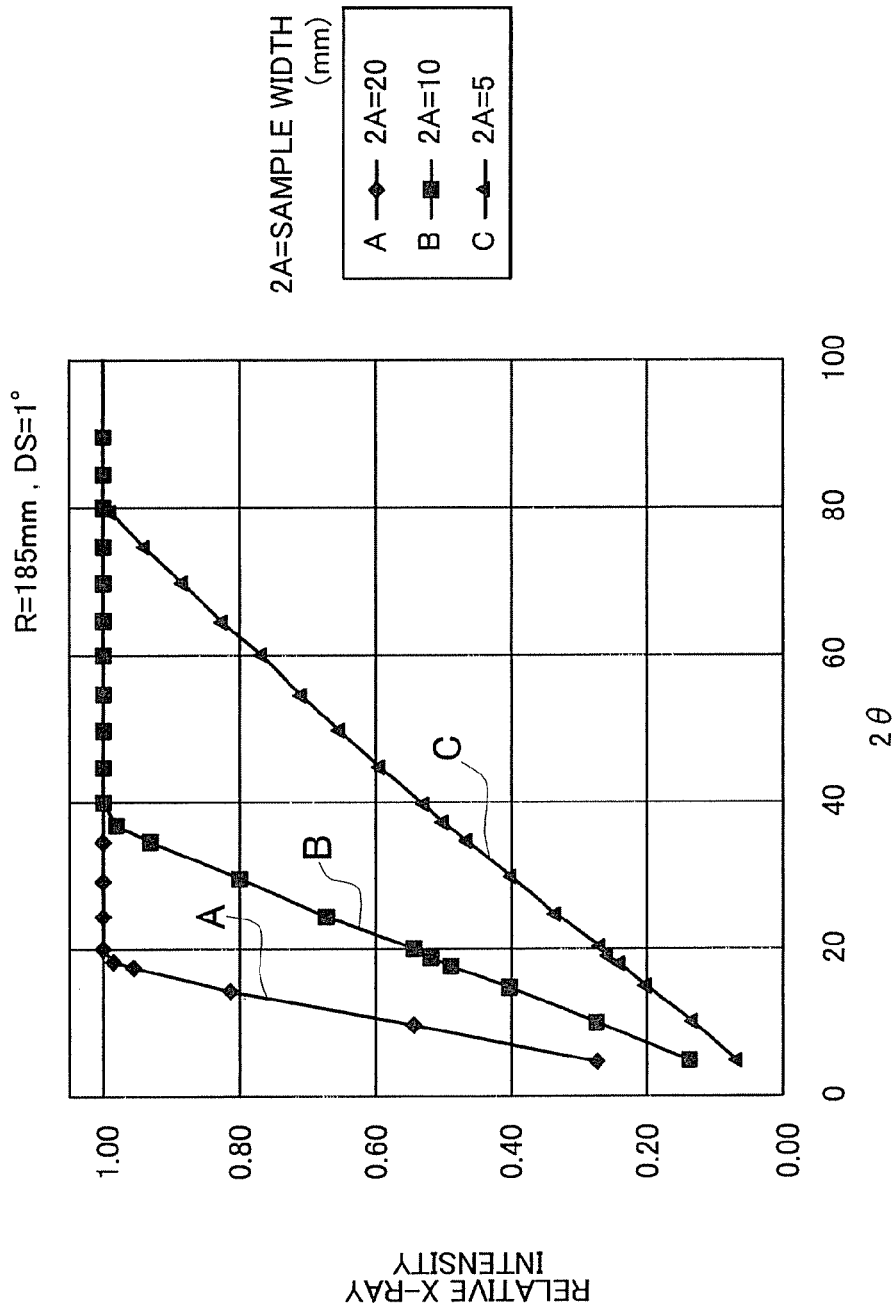
FIG. 14 is a graph showing how the diffracted X-ray intensity changes as varies of diffraction angle $2\theta$.

In the case of the sample of FIG. 8 which is arranged in a longitudinally-elongated manner, the relative X-ray intensity (intensity ratio) is decreased starting from the comparatively high angle side in terms of diffraction angle 2θ as denoted by curves B or C of FIG. 14. Thus, even if measurement data of the diffracted X-ray can be obtained, the obtained data does not have versatility comparable to that of the standard-arrangement sample with which a constant relative X-ray intensity can be obtained. The compensation processing in step S11 of FIG. 5 is performed for compensating such a decrease in the relative X-ray intensity to thereby give versatility to the measurement data.

The intensity compensation will be described below in more detail. Assuming in FIG. 12 that the sample width is "2A", effective divergence angle of the divergence slit 2 calculated from the sample width 2A is "β", effective divergence angle part on the side farther away from the X-ray source F with respect to the sample width center C is "β1", effective divergence angle part on the side nearer to the X-ray source F with respect to the sample width center C is "β2", X-ray incident angle for the sample S is "θ", and radius of the goniometer is "R", the effective divergence angle parts β1 and β2 can be calculated by the following expressions:

$$\tan \beta1 = (\sin \theta)/\{(R/A) - \cos \theta\} \quad (4)$$

$$\tan \beta2 = (\sin \theta)/\{(R/A) + \cos \theta\} \quad (5)$$

and the effective divergence angle β is calculated by $$\beta = \beta1 + \beta2.$$

The CPU performs calculation processing according to the above expressions (4) and (5) to thereby obtain the effective divergence angle parts β1 and β2 for each diffraction angle 2θ.

Subsequently, assuming that the actual divergence angle of the divergence slit 2 is "γ", X-ray intensity calculated based on the output of the X-ray detector 10 is $I_{obs}(\theta)$, and true X-ray intensity is $I_{tru}(\theta)$, the following expression is satisfied:

$$I_{tru}(\theta) = \{\gamma/(\beta1 + \beta2)\} \times I_{obs}(\theta) \quad (6)$$

Thus, the CPU performs calculation for intensity data $I_{obs}(\theta)$ output from the intensity detection circuit 15 of FIG. 1 according to the above expression (6) to thereby compensate X-ray intensity $I_{obs}(\theta)$ so as to obtain true X-ray intensity $I_{tru}(\theta)$.

The compensation using the above expression (6) is effectively used in a region in which the effective divergence angle β of the divergence slit 2 determined based on the sample width 2A of the sample S is smaller than the actual divergence angle γ (that is, region in which each of the effective divergence angle parts β1 and β2 is smaller than the half of the actual divergence angle γ).

To obtain $I_{tru}(\theta)$ corresponding to a fact that a portion of the curve B (sample width 10 mm) or curve C (sample width 5 mm) at which relative X-ray intensity is decreased from right to left is compensated such that relative X-ray intensity=1. As a result, the relative X-ray intensity of diffracted X-ray intensity $I_{tru}(\theta)$ obtained by the compensation maintains a correct constant value in a wide range of the diffraction angle 2θ. Thus, it is possible to perform correct qualitative analysis by comparing the obtained $I_{tru}(\theta)$ with standard data.

Figure 11:
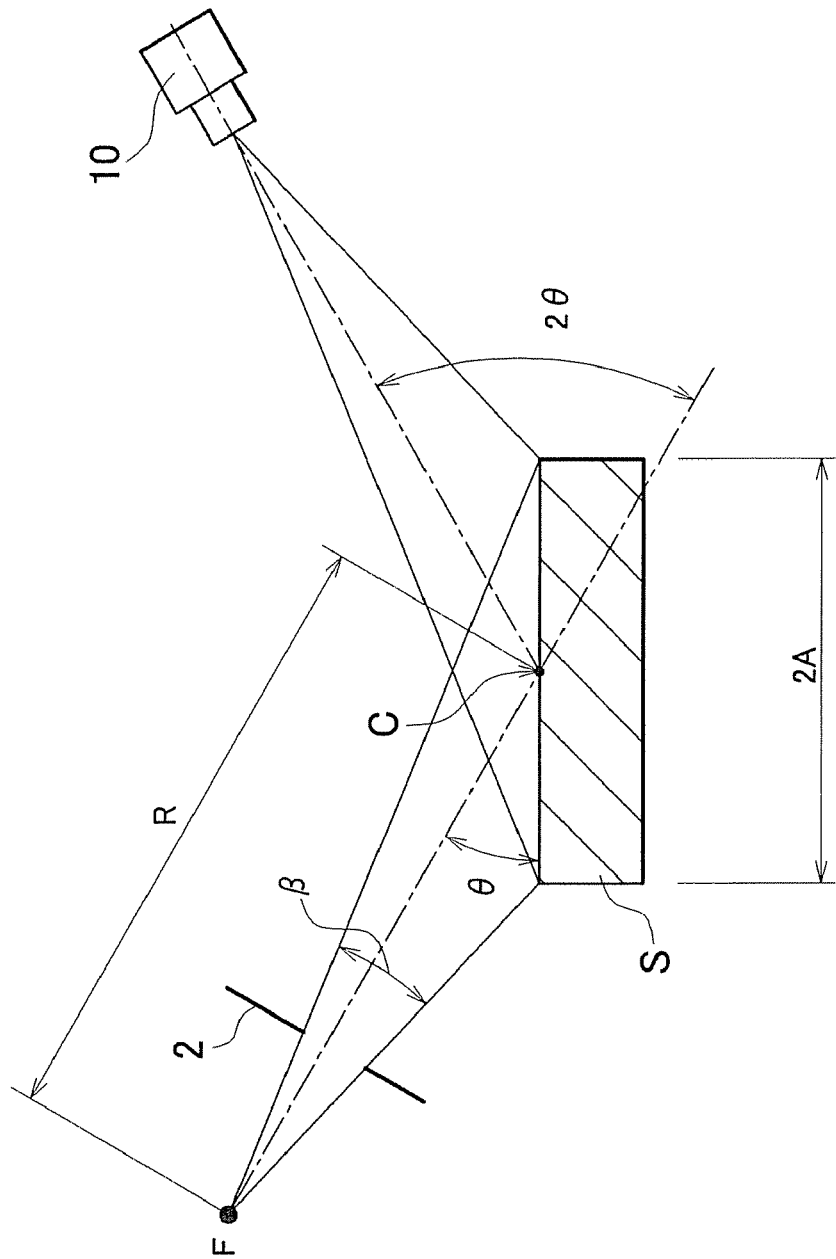
FIG. 11 is a view showing a condition under which effective divergence angle of the divergence slit is calculated based on the sample width.
Figure 12:
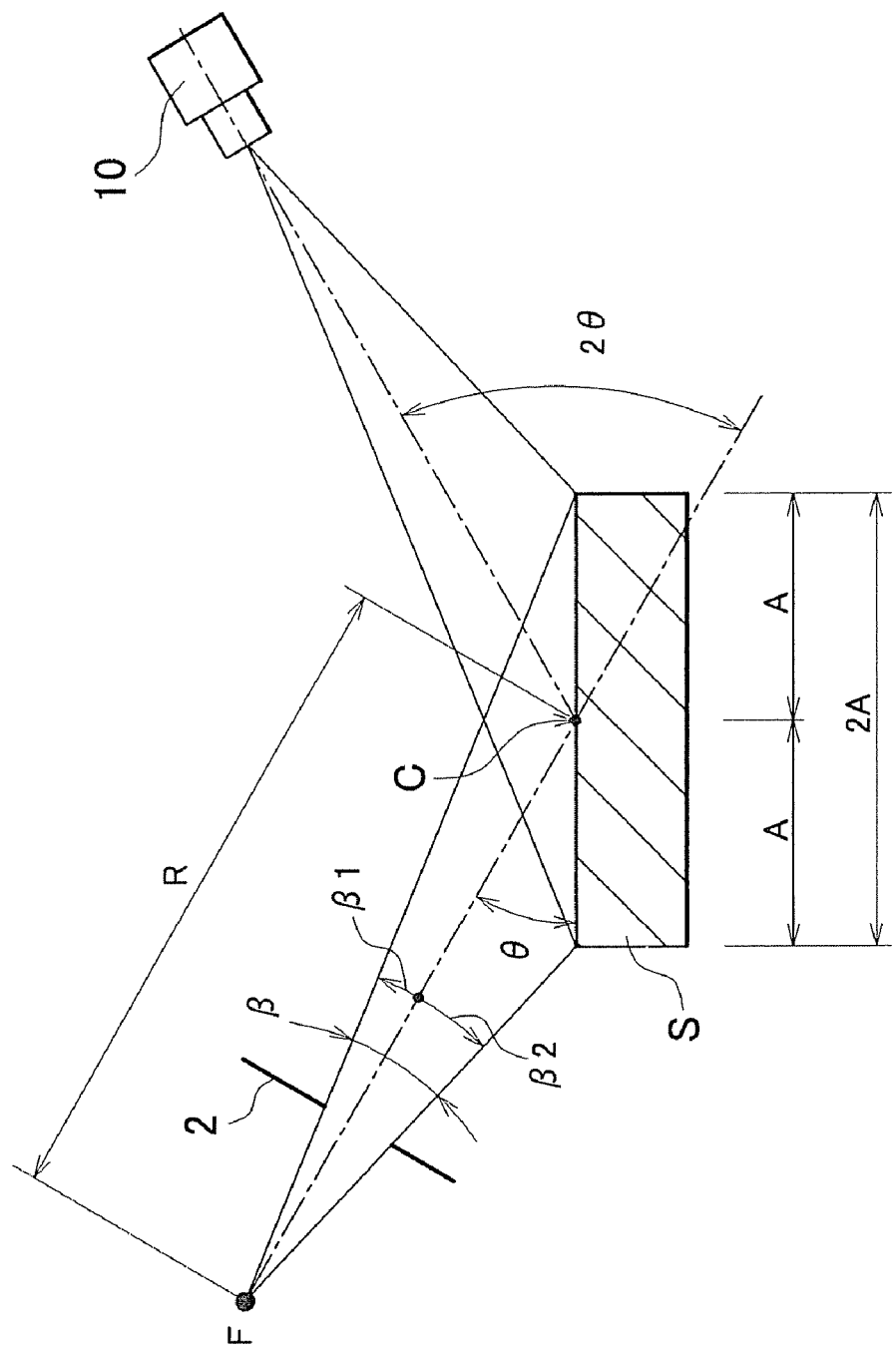
FIG. 12 is a view showing another condition under which effective divergence angle of the divergence slit is calculated based on the sample width.
Figure 13:
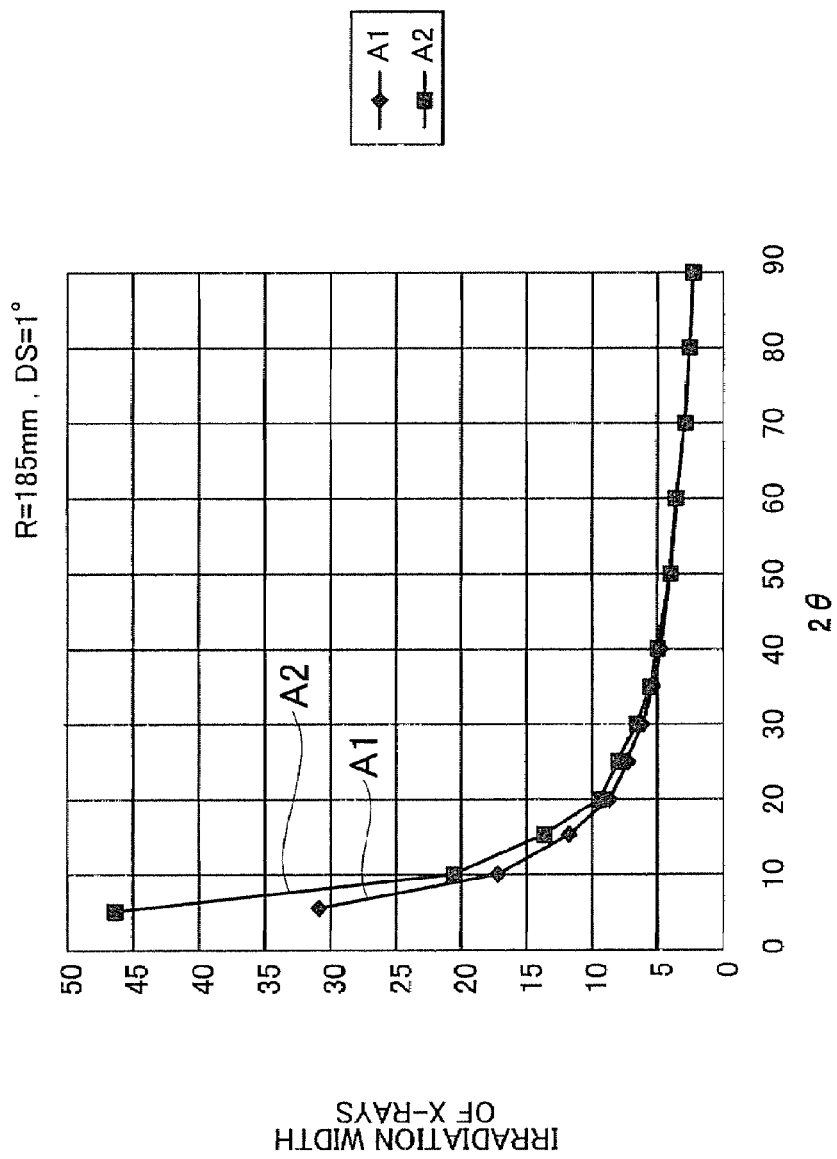
FIG. 13 is a graph showing asymmetric characteristics of the X-ray irradiation width between the right and left parts with respect to the center of sample width.

In the present embodiment, the intensity compensation expression is defined with the sample width 2A separated into two parts of the side away from the X-ray source F and side near the X-ray source F in step S11 of FIG. 5, as shown in FIG. 12. Alternatively, however, the sample width 2A need not be separated in two parts. In this case, as shown in FIG. 11, effective divergence angle β is calculated based on the entire sample width 2A, and measurement data $I_{obs}(\theta)$ is compensated based on the calculated effective divergence angle β.

In this case, effective divergence angle β is calculated based on the sample with 2A according to the following expression:

$$\tan \beta = (\sin \theta)/(R/2A) \qquad (1)$$

and true X-ray intensity $I_{tru}(\theta)$ is calculated according to the following expression:

$$I_{tru}(\theta) = (\gamma/\beta) I_{obs}(\theta) \qquad (2)$$

The compensation using the above expression (2) is effectively used in a region in which the effective divergence angle β of the divergence slit determined based on the sample width of the sample is smaller than the actual divergence angle γ.

As described above, according to the X-ray diffraction apparatus of the present invention, X-ray intensity $I_{obs}(\theta)$ calculated based on the output of the X-ray detector 10 is compensated based on the effective divergence angle of the divergence slit 2 calculated from the sample width of the sample S. This allows a decrease in the relative X-ray intensity (intensity ratio) in the 2θ low angle region, which is exhibited in the sample S arranged in a longitudinally-elongated manner, to be compensated, making it possible to maintain the relative X-ray intensity at a constant value. Thus, when qualitative analysis is performed by comparing a diffraction profile of the sample S having a small sample width with a standard diffraction profile of the sample having the standard sample width, a correct analysis result can be obtained.

Another Embodiment

Although the present invention has been described in its preferred embodiment, it should be understood that the present invention is not limited to the specific embodiment and that various design changes may be made without departing from the scope of the present invention described in the claims.

For example, although the X-ray optical system shown in FIG. 1 is a so-called vertical type goniometer, in which a diffraction surface which is a plane that the X-ray optical axis depicts based on θ-2θ rotation becomes a vertical plane, it is also possible to use a so-called horizontal type goniometer in which the diffraction surface becomes a horizontal plane.

Further, although six sample holders 3 are prepared for the measurement in the above embodiment, the number of types of the sample holders 3 is not limited to six. Further, a concrete value of the sample holder can be changed on a case-by-case basis. In addition, it is possible to change the opening width (that is, sample width) by attaching a non-crystalline solid to the opening of the standard sample holder, eliminating the need to prepare a plurality of sample holders having different sample widths.

In the embodiment shown in FIG. 1, a monochromator (a so-called counter-monochromator) can additionally be provided between the receiving slit 9 and the X-ray detector 10. This monochromator can be made of, for example, graphite. The monochromator guides the diffracted X-ray from the sample S to the X-ray detector 10 by selectively diffracting it to thereby prevent unnecessary X-ray from being captured by the X-ray detector 10. By providing the counter-monochromator, the following advantage can be obtained.

According to the slit compensation of the present embodiment, diffracted X-ray intensity ratio can be measured correctly. However, at the same time, background intensity tends to increase in proportion to the compensation coefficient of the peak intensity. The cause of this is interference by scattering X-ray scattered from an area other than the sample placed on a sample plate. If the counter-monochromator is used to decrease the background of original data, it is possible to reduce the background to a lower level in the data after compensation.

Since the counter-monochromator used here is one having a known configuration, detailed illustration is omitted here. For example, a monochromator disclosed in Japanese Patent Application Laid-Open Publication No. 6-109668 can be used.

EXAMPLE

The present inventor used an X-ray optical system in which the radius R of the goniometer is 150 mm, actual divergence angle of the divergence slit is 1.25°, and sample width 2A is 20 mm to calculate diffracted X-ray intensity $I_{obs}(\theta)$ and further compensated the diffracted X-ray intensity to obtain diffracted X-ray intensity $I_{tru}(\theta)$ As a result, a result shown in FIG. 15 was obtained. In this result, a diffracted X-ray profile B is a profile that has not been subjected to the intensity compensation. A diffracted X-ray profile B is a profile that has been subjected to the intensity compensation.

According to the calculation based on the measurement method shown in FIG. 12 performed under the condition in which goniometer radius R=150 mm, actual divergence angle of the divergence slit=1.25°, and sample width 2A=20 mm, relative X-ray intensity (intensity ratio) was decreased in a region of 2θ<20.08°.

In the result of FIG. 15, the profiles A and B substantially overlap each other in a region in which the diffraction angle 2θ is larger than about 20°. In a region in which the diffraction angle 2θ is smaller than about 20°, an intensity value (A) after compensation is larger than one (B) before compensation. This means that the relative X-ray intensity (intensity ratio) of diffracted X-ray has been compensated, by the present invention, to a correct constant value at the low angle area in which 2θ is about 20°.

What is claimed is:

1. An X-ray diffraction measurement method that irradiates a sample with X-ray emitted from an X-ray source while restricting the X-ray using a divergence slit and detects diffracted X-ray generated from the sample using X-ray detector, wherein
   the divergence angle of the divergence slit is a fixed value,
   the divergence slit is a slit that restricts X-ray irradiation width in the sample width direction,
   the sample is arranged in a longitudinally-elongated manner in which its sample width is smaller than a standard sample width and its sample height is the same as a standard sample height, and
   X-ray intensity calculated based on an output of the X-ray detector is compensated based on an effective divergence angle calculated based on the sample width.

2. The X-ray diffraction measurement method according to claim 1, wherein
   the effective divergence angle "β" is calculated according to the following expression:

$$\tan \beta = (\sin \theta)/(R/2A)$$

where the sample width is "2A", X-ray incident angle for the sample is "θ", and radius of a goniometer is "R", and
   true X-ray intensity $I_{tru}(\theta)$ is calculated according to the following expression:

$$I_{tru}(\theta) = (\gamma/\beta) I_{obs}(\theta)$$

where the actual divergence angle of the divergence slit is "γ" and X-ray intensity calculated based on an output of the X-ray detector is $I_{obs}(\theta)$.

3. The X-ray diffraction measurement method according to claim 1, wherein effective divergence angle part "β1" of the effective divergence angle "β" which is on the side farther away from the X-ray source with respect to the sample width center and effective divergence angle part "β2" of the effective divergence angle "β" on the side nearer to the X-ray source with respect to the sample width center are calculated according to the following expressions:

$$\tan \beta 1 = (\sin \theta)/\{(R/A) - \cos \theta\}$$

$$\tan \beta 2 = (\sin \theta)/\{(R/A) + \cos \theta\}$$

where the sample width is "2A", X-ray incident angle for the sample is "θ", and radius of a goniometer is "R", and true X-ray intensity $I_{tru}(\theta)$ is calculated according to the following expression:

$$I_{tru}(\theta) = \{\gamma/(\beta 1 + \beta 2)\} \times I_{obs}(\theta)$$

where the actual divergence angle of the divergence slit is "γ" and X-ray intensity calculated based on an output of the X-ray detector is $I_{obs}(\theta)$.

4. The X-ray diffraction measurement method according to claim 1, wherein diffracted X-ray generated from the sample is detected by the X-ray detector through a receiving slit and a monochromator, and the monochromator selects X-rays out of diffracted X-rays generated by the sample in wavelength to diffract and lead them to the X-ray detector.

5. The X-ray diffraction measurement method according to claim 2, wherein diffracted X-ray generated from the sample is detected by the X-ray detector through a receiving slit and a monochromator, and the monochromator selects X-rays out of diffracted X-rays generated by the sample in wavelength to diffract and lead them to the X-ray detector.

6. The X-ray diffraction measurement method according to claim 3, wherein diffracted X-ray generated from the sample is detected by the X-ray detector through a receiving slit and a monochromator, and the monochromator selects X-rays out of diffracted X-rays generated by the sample in wavelength to diffract and lead them to the X-ray detector.

7. An X-ray diffraction apparatus comprising:

an X-ray source for emitting X-ray;

a sample holder for supporting a sample;

a divergence slit for guiding X-ray emitted from the X-ray source to the sample by restring the divergence of the X-ray;

an X-ray detector for detecting diffracted X-ray generated from the sample;

an X-ray intensity calculator for calculating X-ray intensity based on an output signal of the X-ray detector, wherein the divergence angle of the divergence slit is a fixed value, the divergence slit is a slit that restricts X-ray irradiation width in the direction of the width of the sample supported by the sample holder, the sample holder supports the sample in a longitudinally-elongated arrangement in which its sample width is smaller than a standard sample width and its sample height is the same as a standard sample height, and the X-ray intensity calculator compensates X-ray intensity $I_{obs}(\theta)$ calculated based on an output of the X-ray detector based on an effective divergence angle calculated based on the sample width to thereby obtain true X-ray intensity $I_{tru}(\theta)$.

8. The X-ray diffraction apparatus according to claim 7, wherein the X-ray intensity calculator calculates the effective divergence angle "β" according to the following expression:

$$\tan \beta = (\sin \theta)/(R/2A)$$

where the sample width is "2A", X-ray incident angle for the sample is "θ", and radius of a goniometer is "R", and calculates true X-ray intensity $I_{tru}(\theta)$ according to the following expression:

$$I_{tru}(\theta) = (\gamma/\beta) I_{obs}(\theta)$$

where the actual divergence angle of the divergence slit is "γ" and X-ray intensity calculated based on an output of the X-ray detector is $I_{obs}(\theta)$.

9. The X-ray diffraction apparatus according to claim 7, wherein the X-ray intensity calculator calculates effective divergence angle part "β1" of the effective divergence angle "β" which is on the side farther away from the X-ray source with respect to the sample width center and effective divergence angle part "β2" of the effective divergence angle "β" on the side nearer to the X-ray source with respect to the sample width center according to the following expressions:

$$\tan \beta 1 = (\sin \theta)/\{(R/A) - \cos \theta\}$$

$$\tan \beta 2 = (\sin \theta)/\{(R/A) + \cos \theta\}$$

where the sample width is "2A", X-ray incident angle for the sample is "θ", and radius of a goniometer is "R", and calculates true X-ray intensity $I_{tru}(\theta)$ according to the following expression:

$$I_{tru}(\theta) = \{\gamma/(\beta 1 + \beta 2)\} \times I_{obs}(\theta)$$

where the actual divergence angle of the divergence slit is "γ" and X-ray intensity calculated based on an output of the X-ray detector is $I_{obs}(\theta)$.

10. The X-ray diffraction apparatus according to claim 7, wherein the X-ray intensity calculator calculates X-ray intensity $I_{obs}(\theta)$ by performing accumulation of an output signal of the X-ray detector at a predetermined sampling time, further calculates true X-ray intensity $I_{tru}(\theta)$ from X-ray intensity $I_{obs}(\theta)$ every time single sampling time has passed, and stores the obtained X-ray intensity $I_{tru}(\theta)$.

11. The X-ray diffraction apparatus according to claim 7, comprising:

a receiving slit provided between the sample holder and the X-ray detector; and a monochromator provided between the receiving slit and the X-ray detector, wherein the monochromator selects X-rays out of diffracted X-rays generated by the sample in wavelength to diffract and lead them to the X-ray detector.

12. The X-ray diffraction apparatus according to claim 8, wherein the X-ray intensity calculator calculates X-ray intensity $I_{obs}(\theta)$ by performing accumulation of an output signal of the X-ray detector at a predetermined sampling time, further calculates true X-ray intensity $I_{tru}(\theta)$ from X-ray intensity $I_{obs}(\theta)$ every time single sampling time has passed, and stores the obtained X-ray intensity $I_{tru}(\theta)$ 13. The X-ray diffraction apparatus according to claim 8, comprising:
    a receiving slit provided between the sample holder and the X-ray detector; and
    a monochromator provided between the receiving slit and the X-ray detector, wherein
    the monochromator selects X-rays out of diffracted X-rays generated by the sample in wavelength to diffract and lead them to the X-ray detector.

14. The X-ray diffraction apparatus according to claim 9, wherein
    the X-ray intensity calculator calculates X-ray intensity $I_{obs}(\theta)$ by performing accumulation of an output signal of the X-ray detector at a predetermined sampling time, further calculates true X-ray intensity $I_{tru}(\theta)$ from X-ray intensity $I_{obs}(\theta)$ every time single sampling time has passed, and stores the obtained X-ray intensity $I_{tru}(\theta)$.

15. The X-ray diffraction apparatus according to claim 9, comprising:
    a receiving slit provided between the sample holder and the X-ray detector; and
    a monochromator provided between the receiving slit and the X-ray detector, wherein
    the monochromator selects X-rays out of diffracted X-rays generated by the sample in wavelength to diffract and lead them to the X-ray detector.

16. The X-ray diffraction apparatus according to claim 12, comprising:
    a receiving slit provided between the sample holder and the X-ray detector; and
    a monochromator provided between the receiving slit and the X-ray detector, wherein
    the monochromator selects X-rays out of diffracted X-rays generated by the sample in wavelength to diffract and lead them to the X-ray detector.

17. The X-ray diffraction apparatus according to claim 14, comprising:
    a receiving slit provided between the sample holder and the X-ray detector; and
    a monochromator provided between the receiving slit and the X-ray detector, wherein
    the monochromator selects X-rays out of diffracted X-rays generated by the sample in wavelength to diffract and lead them to the X-ray detector.

\* \* \* \* \*